(12) United States Patent
Faulhaber

(10) Patent No.: US 11,980,397 B2
(45) Date of Patent: May 14, 2024

(54) ORTHOPEDIC STABILIZATION DEVICES AND METHODS FOR INSTALLATION THEREOF

(71) Applicant: GLOBUS MEDICAL, INC., Audubon, PA (US)

(72) Inventor: Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 172 days.

(21) Appl. No.: 17/589,151

(22) Filed: Jan. 31, 2022

(65) Prior Publication Data

US 2022/0151660 A1    May 19, 2022

Related U.S. Application Data

(63) Continuation of application No. 16/778,469, filed on Jan. 31, 2020, now Pat. No. 11,278,324, which is a continuation of application No. 15/813,207, filed on Nov. 15, 2017, now Pat. No. 10,582,952, which is a continuation of application No. 14/745,519, filed on Jun. 22, 2015, now Pat. No. 9,844,396, which is a continuation of application No. 14/515,626, filed on Oct. 16, 2014, now Pat. No. 9,089,371, which is a continuation of application No. 14/491,125, filed on Sep. 19, 2014, now Pat. No. 9,579,123.

(51) Int. Cl.
*A61B 17/70* (2006.01)
*A61B 17/68* (2006.01)
*A61B 17/86* (2006.01)

(52) U.S. Cl.
CPC ...... *A61B 17/7001* (2013.01); *A61B 17/7032* (2013.01); *A61B 17/7035* (2013.01); *A61B 17/7041* (2013.01); *A61B 17/8625* (2013.01); *A61B 17/8665* (2013.01); *A61B 17/8685* (2013.01); *A61B 2017/681* (2013.01); *A61B 17/7037* (2013.01); *A61B 2017/8655* (2013.01)

(58) Field of Classification Search
CPC .............. A61B 17/86–8695; A61B 17/84–848
USPC .... 606/246–275, 300–321; 623/17.11–17.16
See application file for complete search history.

(56) References Cited

U.S. PATENT DOCUMENTS

| | | | |
|---|---|---|---|
| 4,456,005 A | 6/1984 | Lichty | |
| 5,702,392 A * | 12/1997 | Wu | A61B 17/7043 606/264 |
| 6,565,569 B1 * | 5/2003 | Assaker | A61B 17/7041 606/264 |
| 8,388,660 B1 | 3/2013 | Abdou | |
| 8,454,654 B2 | 6/2013 | Ferragamo | |
| 8,747,472 B2 | 6/2014 | Ainsworth | |
| 8,876,874 B2 | 11/2014 | Abdou | |
| 10,405,893 B2 * | 9/2019 | Laeng | A61B 17/7002 |
| 2004/0092930 A1 * | 5/2004 | Petit | A61B 17/7041 606/279 |

(Continued)

*Primary Examiner* — Matthew J Lawson

(57) ABSTRACT

Embodiments herein are generally directed to fastener or fixation members, such as bone screws, for use in orthopedic stabilization assemblies. Some embodiments herein are directed to a spinal stabilization system or a method of installation of a spinal stabilization system that can include a spinal stabilization anchor including a compressible head, a distal collar separated from the head by a channel, and an elongate, longitudinally-curved shank extending therefrom. The shank further can include at least one friction member.

14 Claims, 19 Drawing Sheets

(56) References Cited

U.S. PATENT DOCUMENTS

| | | |
|---|---|---|
| 2005/0055026 A1* | 3/2005 | Biedermann ........ A61B 17/864 |
| | | 606/328 |
| 2006/0149245 A1 | 7/2006 | Sweeney |
| 2006/0264954 A1 | 11/2006 | Sweeney |
| 2007/0123860 A1* | 5/2007 | Francis .............. A61B 17/7049 |
| | | 606/250 |
| 2009/0306718 A1 | 12/2009 | Tipirneni |
| 2010/0016903 A1 | 1/2010 | Matityahu |
| 2010/0076498 A1 | 3/2010 | Tyber |
| 2011/0054545 A1 | 3/2011 | Champagne |
| 2011/0174472 A1 | 7/2011 | Kurochkin |
| 2011/0288588 A1* | 11/2011 | Chin .................... A61B 17/866 |
| | | 606/264 |
| 2012/0059428 A1 | 3/2012 | Epperly |
| 2012/0172936 A1* | 7/2012 | Horrell .............. A61B 17/0401 |
| | | 606/104 |
| 2013/0041414 A1 | 2/2013 | Epperly |
| 2013/0053902 A1 | 2/2013 | Trudeau |
| 2013/0131733 A1 | 5/2013 | Chien |
| 2014/0012336 A1 | 1/2014 | Biedermann |
| 2014/0257408 A1 | 9/2014 | Trieu |
| 2015/0012051 A1 | 1/2015 | Warren |

\* cited by examiner

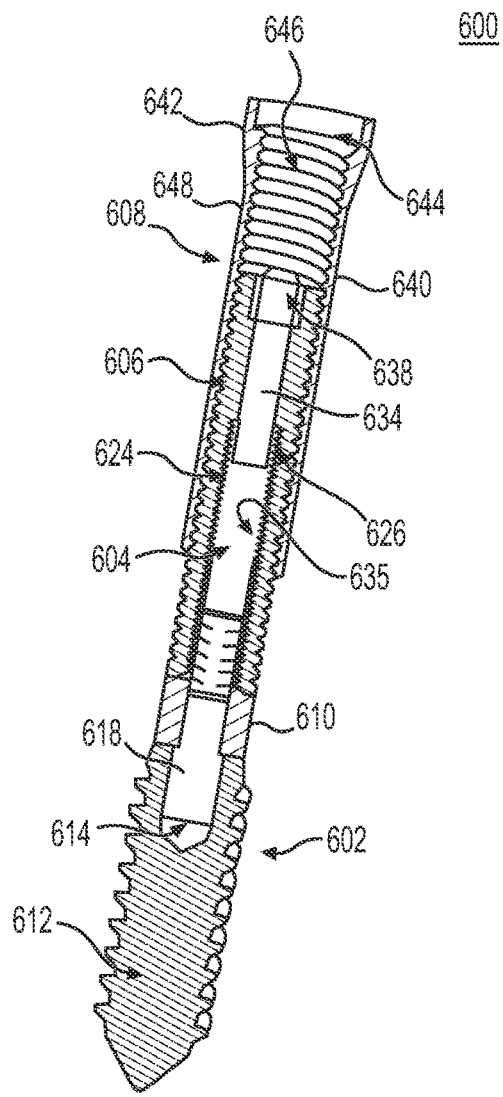
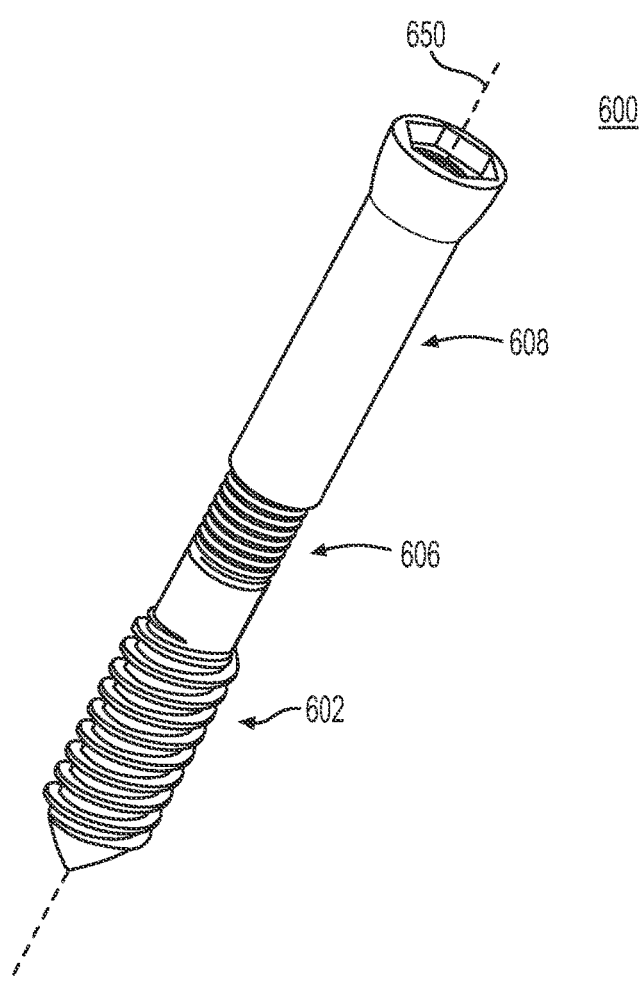
FIG. 15A
FIG. 15B

ORTHOPEDIC STABILIZATION DEVICES AND METHODS FOR INSTALLATION THEREOF

CROSS-REFERENCE TO RELATED APPLICATION

The present application is a continuation of U.S. patent application Ser. No. 16/778,469, filed on Jan. 31, 2021 (published as U.S. Pat. Pub. No. 2020-0163700), which is a continuation of U.S. patent application Ser. No. 15/813,207, filed Nov. 15, 2017, now U.S. Pat. No. 10,582,952, which is a continuation of U.S. patent application Ser. No. 14/745,519, filed Jun. 22, 2015, now U.S. Pat. No. 9,844,396, which is a continuation of U.S. patent application Ser. No. 14/515,626, filed Oct. 16, 2014, now U.S. Pat. No. 9,089,371, which is a continuation of U.S. patent application 14/491,125, filed Sep. 19, 2014, now U.S. Pat. No. 9,579,123, the contents of which are hereby incorporated by reference in their entireties for all purposes.

FIELD OF THE INVENTION

The present invention relates to orthopedic stabilization devices and methods used to install these devices.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of fixation devices to one or more vertebrae and connecting the devices to an elongate rod that generally extends along the length of the spine.

Treatment for these spinal irregularities often involves using a system of fixation devices to attain stability between spinal segments. Instability in the spine can create stress and strain on neurological elements, such as the spinal cord and nerve roots. In order to correct this, various implants can be used to restore the correct alignment and position of the vertebral bodies. In some cases, a stabilization device, optionally in conjunction with a vertical solid member, can help restore and/or correct the alignment of spinal segments, thereby reducing pain or preventing further injury to the spine.

Stabilization devices may include a bone fastener, such as a screw, for fastening the device to vertebra. Some stabilization devices further may include a coupling element (e.g., a tulip element) for coupling the bone fastener to the vertical solid member (e.g., elongate rod). Clamp and/or wedge elements may be used to secure the bone fastener in the coupling element. A locking cap may also be used to secure the rod in the coupling element.

SUMMARY OF THE INVENTION

Some embodiments herein are directed to a spinal stabilization anchor that can include a compressible head; a distal collar separated from the head by a channel; and an elongate, longitudinally-curved shank extending therefrom and comprising at least one friction member.

Other embodiments herein are directed to a spinal stabilization system that can include a spinal stabilization anchor comprising a compressible head, a distal collar separated from the head by a channel, and an elongate, longitudinally-curved shank extending therefrom, wherein the shank further comprises at least one friction member; and a fastener member comprising a threaded shaft having a distal tip configured to be pivotably coupled to the spinal stabilization anchor.

Some embodiments herein are directed to a method of installing a spinal stabilization assembly that can include inserting a spinal stabilization anchor into a bone, wherein the spinal stabilization anchor includes a compressible head, a distal collar separated from the head by a channel, and an elongate, longitudinally-curved shank extending therefrom, wherein the shank further comprises at least one friction member; inserting a fastener member into the bone, wherein the fastener member comprises a threaded shaft having a distal tip configured to be pivotably coupled to the spinal stabilization anchor; and coupling the fastener member to the spinal stabilization anchor by inserting the compressible head into the distal tip.

Other embodiments herein are directed to a spinal stabilization system that can include a fastener member comprising a threaded shank and a head; an elevation member configured to be disposed on the fastener member and configured to adjust a length of the spinal stabilization system; a coupling member configured to couple the fastener member to a rod and comprising a rod-receiving channel and a proximal end with interior threading; and a set screw configured to mate with the proximal end of the coupling member.

Some embodiments herein are directed to a fastener member comprising a threaded shank and a threaded head, the threaded head further comprising a socket; an elevation member comprising a body having a proximal face, a distal face, a threaded hole extending therethrough and configured to mate with the threaded head, and a first connector member; a coupling member comprising: an upper portion having two arms defining a rod-receiving channel, and a lower portion having a stem and at a second connector member, wherein the stem is configured to be wedged in the socket of the fastener member and the second connector member is configured to mate with the first connector member; and a locking member configured to engage the upper portion of the coupling member.

Other embodiments herein are directed to a spinal stabilization system that can include a fastener member comprising a threaded shank extending longitudinally from a threaded head, the threaded head further comprising a socket; a gear member comprising an outer surface with a plurality of teeth, a threaded hole configured to mate with the threaded head, and a proximal surface having a receptacle thereon; a coupling member comprising: an upper portion configured to receive a rod; and a lower portion having a stem configured to be keyed in the socket of the fastener member and a slotted collar having a lip configured to be received in the receptacle; and a locking member configured to engage the upper portion of the coupling member.

Some embodiments herein are directed to a method of installing a spinal stabilization system that can include providing a spinal stabilization system comprising: a fastener member comprising a threaded shank extending longitudinally from a threaded head, the threaded head further comprising a socket; a gear member comprising an outer surface with a plurality of teeth, a through bore with internal threading mated with the threaded head, and a proximal surface having a receptacle thereon; a coupling member comprising: an upper portion configured to receive a rod, and a lower portion having a stem keyed in the socket of the fastener member and a slotted collar having a lip received in the channel surrounding the through bore; and a locking member configured to engage the upper portion of the coupling member; engaging the locking member with the proximal end of the coupling member to secure a rod in the rod-receiving channel; and adjusting a position of the coupling member along a longitudinal axis of the system after the rod is secured in the rod-receiving channel.

Other embodiments herein are directed to a spinal stabilization system that can include a fastener assembly, comprising: a fastener member comprising a threaded shank extending longitudinally from a threaded head, the threaded head further comprising a socket; and a compression member comprising a rounded head, an elongate body, and a longitudinal bore extending therethrough, wherein a portion of the longitudinal bore in the rounded head comprises a socket, and a portion of the longitudinal bore in the elongate body is configured to engage the head of the fastener member; and a clamp assembly, comprising: a clamp member comprising a rounded inner surface configured to receive the rounded head of the compression member, a rounded outer surface, and an opening configured to receive the elongate body of the compression member therethrough; a coupling member comprising: a rod-receiving portion comprising a channel, a fastener-receiving portion comprising an aperture having a rounded interior surface configured to receive the clamp member, and a locking portion comprising a first locking receptacle; and a first locking member configured to be received within the first locking receptacle of the coupling member.

Some embodiments herein are directed to a spinal stabilization system that can include a pedicle screw assembly, comprising: a fastener member comprising a threaded shank extending longitudinally from a threaded post, the threaded post further comprising a socket; and a compression nut comprising a rounded head, an elongate body, and a longitudinal bore extending therethrough, wherein a portion of the longitudinal bore in the rounded head comprises a socket configured to receive a driver, and a portion of the longitudinal bore in the elongate body comprises threading configured to mate with the threaded post of the fastener member; and a polyaxial clamp assembly, comprising: a clamp member comprising a rounded inner surface configured to receive the rounded head of the compression nut, a rounded outer surface, and an opening configured to receive the elongate body of the compression nut therethrough; a rod-locking member; a fastener-locking member; and a coupling member comprising: a rod-receiving channel, a first receptacle configured to receive the rod-locking member, a through bore having a rounded interior surface and configured to receive the clamp member, and a second receptacle configured to receive the fastener-locking member.

Other embodiments herein are directed to a method of installing a spinal stabilization system that can include providing an assembled spinal stabilization system that can include a coupling member comprising: a rod-receiving portion comprising a channel, a fastener-receiving portion comprising an aperture having a rounded interior surface, and a locking portion comprising a first locking receptacle; a clamp member disposed in the aperture of the fastener-receiving portion, the clamp member comprising a rounded inner surface, a rounded outer surface, a chamber, and an opening configured to receive the elongate body of the compression member therethrough; a first locking member disposed in the first locking receptacle of the coupling member; a compression member comprising a rounded head disposed in the chamber, and further comprising an elongate body and a longitudinal bore extending therethrough, wherein a portion of the longitudinal bore in the rounded head comprises a socket, and a portion of the longitudinal bore in the elongate body is configured to engage the head of the fastener member; and a fastener member threaded into the longitudinal bore of the compression member and comprising a threaded head and a threaded shank extending longitudinally from the threaded head. These embodiments can also include driving the fastener member into a bone; inserting a rod into the channel; adjusting a position of the clamp assembly along a longitudinal axis, after the rod is inserted into the channel; threading the first locking member into the first locking receptacle and over the securing member to secure the fastener assembly at an angle relative to the clamp assembly; and threading the second locking member into the second locking receptacle to secure the rod in the channel.

Some embodiments herein are directed to a spinal stabilization system that can include a screw comprising a post, a threaded shank extending distally from the post, and a socket; a torsion shaft comprising: a distal section configured to be received within the socket; a body comprising at least one cut; and a proximal section comprising an externally-threaded portion and a tool-receiving recess; a relief screw comprising a body having an externally-threaded portion, a proximal end having a tool-receiving recess, and a bore extending longitudinally therethrough, wherein the bore comprises an internally-threaded section configured to mate with the externally-threaded section of the torsion shaft; and a compression nut comprising a proximal end having a tool-receiving recess, a body, and a bore extending longitudinally therethrough, wherein the bore comprises an internally-threaded portion configured to mate with the externally-threaded body of the relief screw.

Other embodiments herein are directed to a spinal stabilization system that can include a fastener member comprising a head, a threaded body extending longitudinally from the head, and a socket; a torsion member comprising: a distal section configured to be received within the socket, a flexible body, and a proximal section comprising an externally-threaded portion and a tool-receiving recess; a relief member comprising a bore extending longitudinally therethrough, a body comprising external threading, and a proximal end having a tool-receiving recess, wherein the bore comprises an internally-threaded portion configured to mate with the externally-threaded portion of the torsion member; and a compression member comprising a proximal end having a tool-receiving recess and a bore extending longitudinally therethrough, wherein the bore comprises an internally-threaded portion configured to mate with the external threading of the relief member.

Some embodiments herein are directed to a spinal stabilization system that can include a fastener member comprising a head, a threaded body extending longitudinally from the head, and a socket; a torsion member comprising a distal section, a flexible body, and a proximal section comprising an externally-threaded segment and a tool-receiving recess, wherein at least the distal section is disposed within the socket of the fastener member; a relief member comprising a body comprising external threading and a bore extending longitudinally therethrough, wherein the bore comprises a proximal end having a tool-receiving recess and an internally-threaded portion engaged with the externally-threaded portion of the torsion member; and a compression member comprising an bore extending longitudinally therethrough and a proximal end having a tool-receiving recess, wherein the bore comprises a threaded portion engaged with the external threading of the relief member.

Other embodiments herein are directed to a method of installing a spinal stabilization system that can include providing an assembled spinal stabilization system; creating a passageway through a proximal bone and a distal bone, wherein the passageway has a diameter that is smaller in the distal bone than in the proximal bone; driving the threaded body of the fastener member through the passageway into the distal bone; and driving the compression member through the passageway into the proximal bone to alter the relative alignment between the bones.

Further areas of applicability of the present invention will become apparent from the detailed description provided hereinafter. It should be understood that the detailed description and specific examples, while indicating certain embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4A illustrates a perspective view of one embodiment of a fastener member as disclosed herein;

FIG. 4B illustrates a perspective view of an elevation member coupled to a fastener member;

FIGS. 4C-D illustrate perspective views of a coupling member, elevation member, and fastener member;

FIGS. 11A-C illustrate installed spinal stabilization systems;

FIGS. 15A-B illustrate a cross-sectional view and a perspective view of an assembled spinal stabilization system;

DETAILED DESCRIPTION

Spinal stabilization devices, such as screw-based systems, may be used to correct or restore vertebral alignment. Using these types of systems, one or more screws may be implanted in the affected vertebrae. In some instances, the screw may loosen and/or back out of the vertebrae over time and the screw placement may need to be revised, e.g., in a subsequent surgical procedure. This may happen, for example, if the screw was placed in osteoporotic bone. One method for revising the screw placement can include removing the old screw and implanting a larger screw, which may be effective at gripping the bone, but which may also reduce the overall structural stability of the bone. Furthermore, a subsequent surgical procedure can present other additional risks to a patient. Accordingly, disclosed herein are new and improved spinal stabilization devices that can increase stability of the interface between a bone and a screw in the cancellous region of a vertebral body, reduce the tendency of a screw to loosen and/or back out, and/or reduce the diameter of a screw used in a revision procedure.

Some screw-based systems include a plurality of screws inserted into the pedicles of adjacent vertebrae and coupled to an elongate rod. In some procedures (e.g., to correct a spinal deformity), screws and rods may be implanted that extend along a significant length of a spine. In these types of procedures, as well as others utilizing a smaller number of screws and/or rods, it can be difficult to align all of the screws at a proper depth to securely couple with the rod(s). Accordingly, disclosed herein are new and improved spinal stabilization devices that allow the depth of a screw to be adjusted after it is coupled to a rod, and/or without needing to drive the screw further into or out of a vertebra.

Various devices, such as pedicle screw systems and/or intervertebral cages, may be used to treat spondylolisthesis, a condition in which one or more vertebrae are displaced in the anterior direction. Advantageously, disclosed herein are new and improved spinal stabilization devices that can correct vertebral displacement using a single screw, and optionally, in a minimally-invasive procedure. Components of all of the spinal stabilization devices disclosed herein can be made of materials known to those skilled in the art, including metals (e.g., titanium), metal alloys, polymers (e.g., PEEK), allograft, and/or combinations thereof. The components can also be machined and/or manufactured using techniques known to those skilled in the art.

Figure 1A:
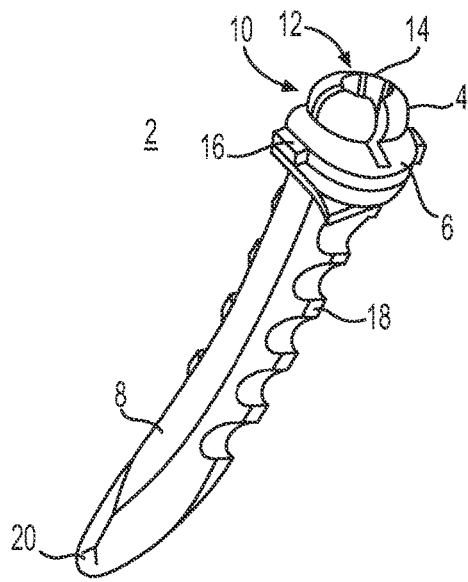
FIGS. 1A-B illustrate perspective views of one embodiment of a spinal stabilization anchor as disclosed herein.
Figure 1B:
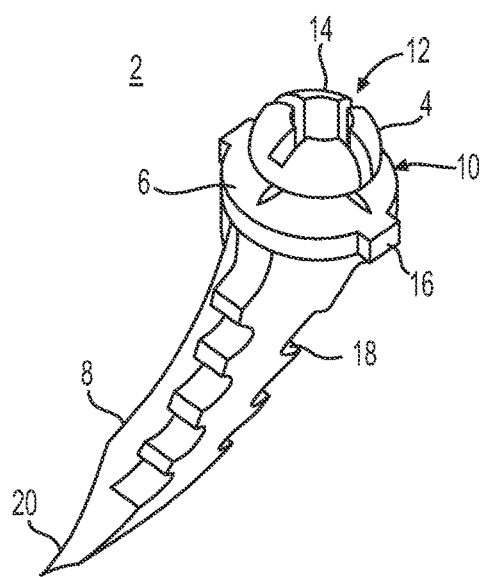

Turning now to FIGS. 1A-B, a perspective view of a spinal stabilization anchor 2 is illustrated in accordance with embodiments described herein. As illustrated, the spinal stabilization anchor 2 may include a head 4, a collar 6, a shank 8, and a channel 10. In some embodiments, the spinal stabilization anchor 2 may be referred to as a spike or nail. The head 4 can be rounded. In some embodiments, at least a portion of the head 4 may be compressible (e.g., the diameter of a rounded head 4 may be reversibly reduced upon application of force). The head 4 may be compressible as the result of various materials and/or features. For example, in some embodiments the head 4 can include at least one slot 12. As illustrated in FIGS. 1A-B, the head 4 can include four slots. The head 4 can further include a tool-receiving socket 14. The tool-receiving socket 14 can be configured to receive a driver or other insertion tool.

As illustrated in FIGS. 1A-B, the collar 6 can include one or more alignment members, such as protrusions 16. The protrusions 16 can advantageously be used to align or guide the spinal stabilization anchor 2 during the installation process. In other embodiments, the collar 6 may include grooves, slots, or other features to assist with installation. As illustrated in FIGS. 1A-B, the collar 6 may be positioned distal to the head 4, and may be separated from the head 4 by channel 10. The channel 10 can surround the head 4.

As illustrated in FIGS. 1A-B, the shank 8 extends distally from the collar 6 and can have an elongated shape, terminating in a distal tip 20. The distal tip 20 can take on any shape, such as sharp, pointed, or blunt. The shank 8 may be curved along a longitudinal axis. Accordingly, as illustrated in FIGS. 1A-B, the pointed distal tip can be laterally displaced relative to the head 4. In other embodiments, the distal tip 20 may be laterally displaced relative to the head 4 by angling away from the head 4, instead of curving away from the head 4.

The shank 8 can also include at least one friction member 18 disposed thereon. As illustrated in FIGS. 1A-B, the shank 8 may include a plurality of friction members, such as teeth, bumps, or ratcheting. In some embodiments, the shank 8 may include one, two, or more rows of friction members. For example, as illustrated in FIGS. 1A-B, the shank 8 can include two rows of teeth. One or more friction members 18 may be angled towards the proximal end of the spinal stabilization anchor 2, so as to advantageously prevent or reduce the backing out of the anchor 2 from a bone.

Figure 2A:
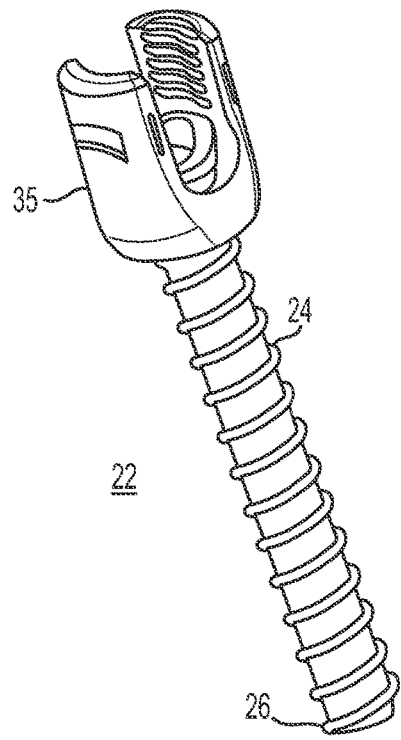
FIG. 2A illustrates a perspective view of one embodiment of a fastener member as disclosed herein.

Some embodiments herein are directed to a spinal stabilization system 100. The spinal stabilization system 100 can include the spinal stabilization anchor 2 and a fastener member 22, illustrated in FIGS. 2A-C. In some embodiments, the fastener member 22 may be a bone screw, such as a pedicle screw and/or a compression screw. For example, the fastener member 22 may be any of the bone screws described herein. Additionally, although illustrated with a rod-coupling member 35 in FIG. 2A, those skilled in the art may appreciate that the rod-coupling member 35 is an optional component of the assembly.

Figure 2B:
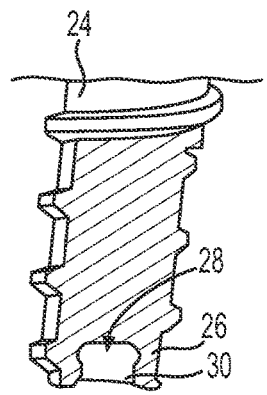
FIG. 2B is a partial cross-section view of a distal end of the fastener member illustrated in FIG. 2A.
Figure 2C:
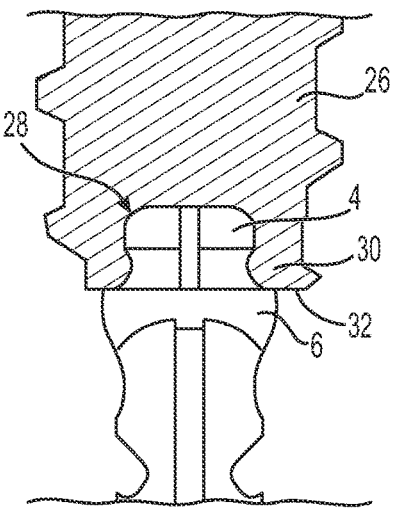
FIG. 2C is a partial cross-section view of a spinal stabilization anchor coupled to a fastener member.

The fastener member 22 can include a threaded shaft 24 and a distal tip 26. The distal tip 26 can be configured to be pivotably coupled to the spinal stabilization anchor 2. As illustrated in FIGS. 2B-C, the distal tip 26 can include a recess 28 that is configured to receive the head 4. In embodiments where the head 4 is rounded, the recess 28 may also have a rounded interior surface which corresponds to the shape of the head 4. The distal tip 26 can also include a lip 30 that is configured to be received in the channel 10 of the spinal stabilization anchor 2. As illustrated in FIG. 2C, the collar 6 may function as a ledge upon which at least a portion of the distal-most surface 32 of the distal tip 26 may rest.

Embodiments herein are also directed to methods of installing the spinal stabilization system 100 described herein. Those skilled in the art may appreciate that the spinal stabilization anchor 2 and fastener member 22 may be installed in a variety of different bones, including the various vertebrae as well as other non-vertebral bones. Additionally, the spinal stabilization anchor 2 may be inserted into a bone using any means known to those skilled in the art.

Figure 3A:
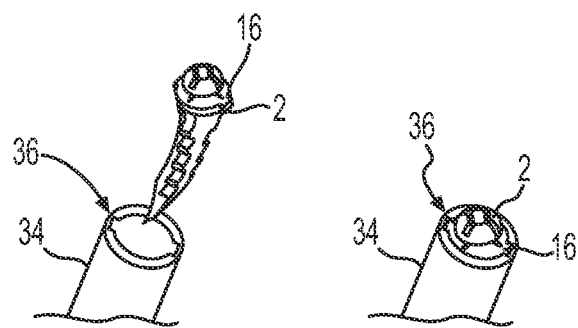
FIGS. 3A-E are perspective views, in partial cross-section, of one method of installing a spinal stabilization system as disclosed herein.
Figure 3A:
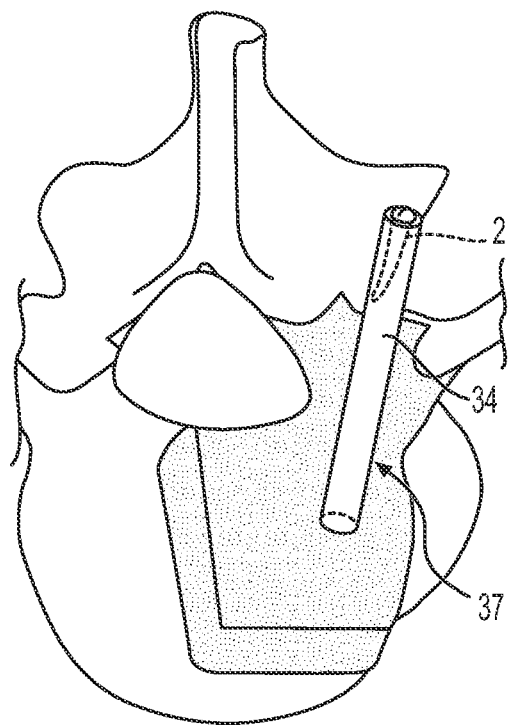

In one example, prior to installing the spinal stabilization anchor 2, the installation site may be prepared by creating (e.g., drilling) a hole 37 through which the spinal stabilization anchor 2 may pass. As illustrated in FIG. 3A, the hole 37 may be formed in a posterior section of a vertebra; however, the exact position can vary depending on the particular procedure being performed.

Figure 3B:
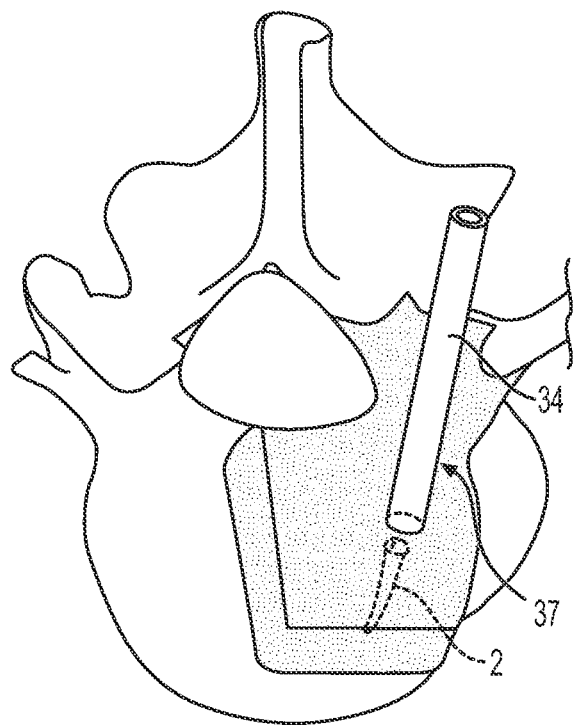

Once the hole 37 is formed, the spinal stabilization anchor 2 may be inserted through the hole 37 and into the bone, as illustrated in FIGS. 3A-B. The spinal stabilization anchor 2 may be inserted into any portion of the bone as appropriate for the particular procedure. In some embodiments, the spinal stabilization anchor can be inserted into a cancellous region of the bone.

In some embodiments, the spinal stabilization anchor 2 may be inserted directly through the hole 37. In other embodiments, as illustrated in FIGS. 3A-B, the spinal stabilization anchor 2 can be inserted through a cannula or sleeve 34 to the bone. Optionally, the sleeve 34 may include one or more alignment members 36. As illustrated in FIG. 3A, the alignment member 36 can be a groove that is configured to accept the protrusion 16 on the collar 6 of the spinal stabilization anchor 2. In some embodiments, the step of inserting the spinal stabilization anchor 2 into the bone can further include securing the spinal stabilization anchor 2 into the bone using a linear force. For example, the spinal stabilization anchor 2 may be hammered into the bone.

Figure 3C:
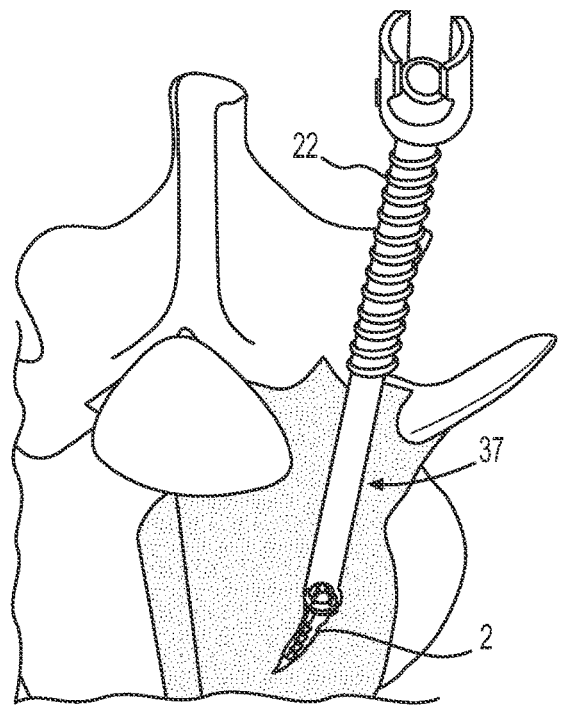

Once the spinal stabilization anchor 2 is secure, the fastener member 22 may be inserted into the bone. As illustrated in FIG. 3C, the fastener member 22 may be inserted into the same hole through which the spinal stabilization anchor 2 was passed. In some embodiments, the fastener member 22 may pass directly through the hole. In other embodiments, the fastener member 22 may be inserted through a cannula or sleeve.

Figure 3D:
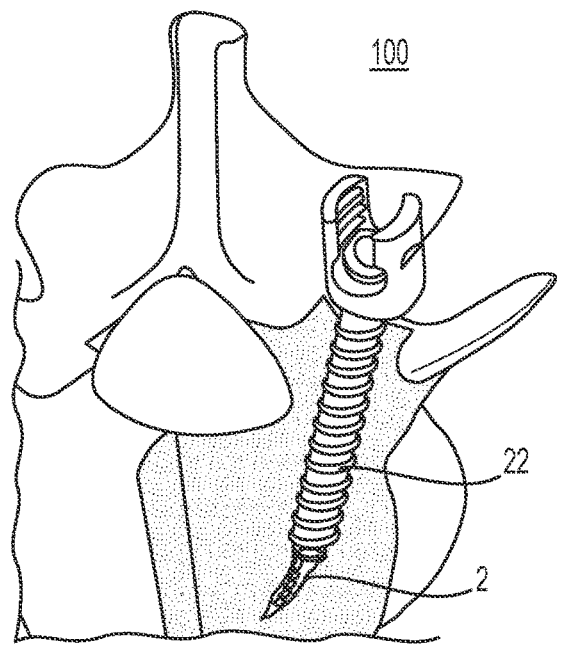
Figure 3E:
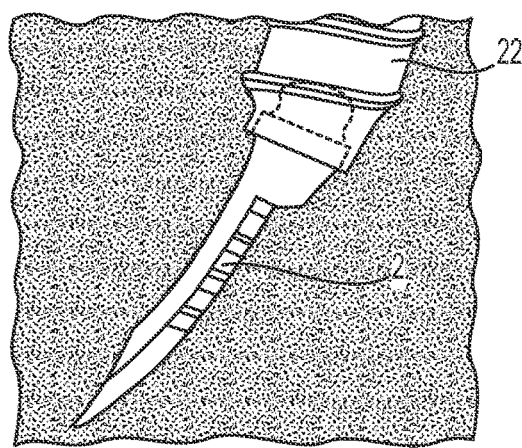

After the spinal stabilization anchor 2 and the fastener member 22 have been inserted, they may be coupled to each other, as illustrated in FIG. 3D-E. As illustrated in FIG. 2C, the coupling step may include inserting the head 4 of the spinal stabilization anchor 2 into the recess 28 of the distal tip 26 of the fastener member 22. In use, the fastener member 22 may be coupled, hitched, or connected to the spinal stabilization anchor 2 by applying a linear force, e.g., by pushing, the distal tip 26 onto the head 4. This pressure may cause the head 4 to compress and enter the recess 28 of the distal tip 26, where the head 4 may expand. The lip 30 may advantageously prevent the head 4 from backing out of the recess 28. While the head 4 of the spinal stabilization anchor 2 is disposed within the recess 28 of the fastener member 22, the fastener member 22 may advantageously be pivotable about the spinal stabilization anchor 2. In some embodiments, the head 4 of the spinal stabilization anchor 2 and the recess 28 of the fastener member 22 may function like a ball and socket joint.

As described herein, fastener members, such as pedicle screws and other bone screws, may occasionally move back and forth within a bone, eventually enlarging the hole and causing the fastener members to loosen or back out from the vertebra within which they were implanted. Among other reasons, this phenomenon, sometimes referred to as the "windshield wiper effect," may be the result of being implanted in bone that is particularly porous, weak, and/or lacking sufficient density. When the fastener members come loose, the structural integrity of the overall construct may be affected. In some instances, revision surgery is used to correct this loosening, for example, but replacing the original screw with a larger screw.

Advantageously, the spinal stabilization anchor 2 described herein can reduce the likelihood that a fastener member will loosen or back out from a vertebral body by increasing the stability of the interface between the fastener member and the vertebral body. Those skilled in the art may appreciate that the interface between the coupled spinal stabilization anchor 2 and the fastener member 22, as illustrated in FIG. 2C, can allow the fastener member 22 to pivot relative to the spinal stabilization anchor 2. If the fastener member 22 moves back and forth within a bone, it may pivot relative to the spinal stabilization anchor 2 without backing out from the bone.

Additionally, the spinal stabilization anchor 2 and fastener member 22 described herein may be used advantageously in a revision procedure. As described herein, one method of performing a revision procedure may include removing the existing fastener member and inserting a new fastener member having a larger diameter to be secured within the enlarged hole created by the windshield wiper effect. However, a larger diameter fastener member may not be required when using the devices described herein, since the fastener member 22 can be secured to a bone by virtue of being coupled to the spinal stabilization anchor 2, rather than relying solely on being secured within the enlarged hole.

Figure 6A:
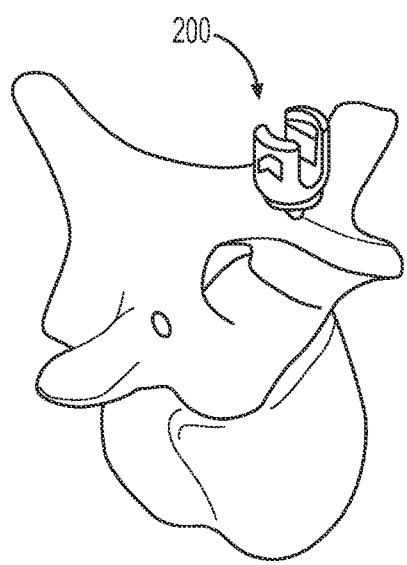
FIGS. 6A-F illustrate perspective views of one method of installing a spinal stabilization anchor as disclosed herein.

Turning now to FIGS. 4A-D, a perspective view of various components of a spinal stabilization system 200 is illustrated in accordance with embodiments described herein. As illustrated in FIGS. 4A-D, the spinal stabilization system 200 can include a fastener member 202, an elevation member 204, and a coupling member 206. In some embodiments, the spinal stabilization system 200 can further include a locking member 208, as illustrated in FIG. 6F.

As illustrated in FIG. 4A, the fastener member 202 can include a threaded shank 210 and a head 212. The threaded shank 210 may extend longitudinally from the head 212. In some embodiments, the fastener member 202 can be monolithic. In some embodiments, the head 212 can be threaded (e.g., can include exterior and/or interior threading). Additionally, in some embodiments, the head 212 can include a socket 214. In some embodiments, the head 212 can include a cylindrical (e.g., constant diameter) outer surface. For example, in some embodiments the head 212 may be referred to as a post. In some embodiments where the head 212 includes exterior threading, the threaded head can include a constant major thread diameter and/or a constant minor thread diameter. In embodiments where the head 212 is cylindrical and includes exterior threading, it may be referred to as a threaded post. In some embodiments, the fastener member 202 may be referred to as a posted screw. In some embodiments, the fastener member 202 may be a pedicle screw, such as a monoaxial or polyaxial pedicle screw. The socket 214 can be configured to receive a driver, such as a screwdriver or a hex key. As described further herein, the socket 214 can also be configured to receive a portion of the coupling member 206. The lateral cross-sectional shape of the socket 214 can vary to accommodate various drivers, and can be, for example, a slot, cross, star, triangle, square, hexagon, or pentagon. In some embodiments, at least a section of the socket 214 can have a hexagonal lateral cross-section, as illustrated in FIG. 4A.

Figure 4D:
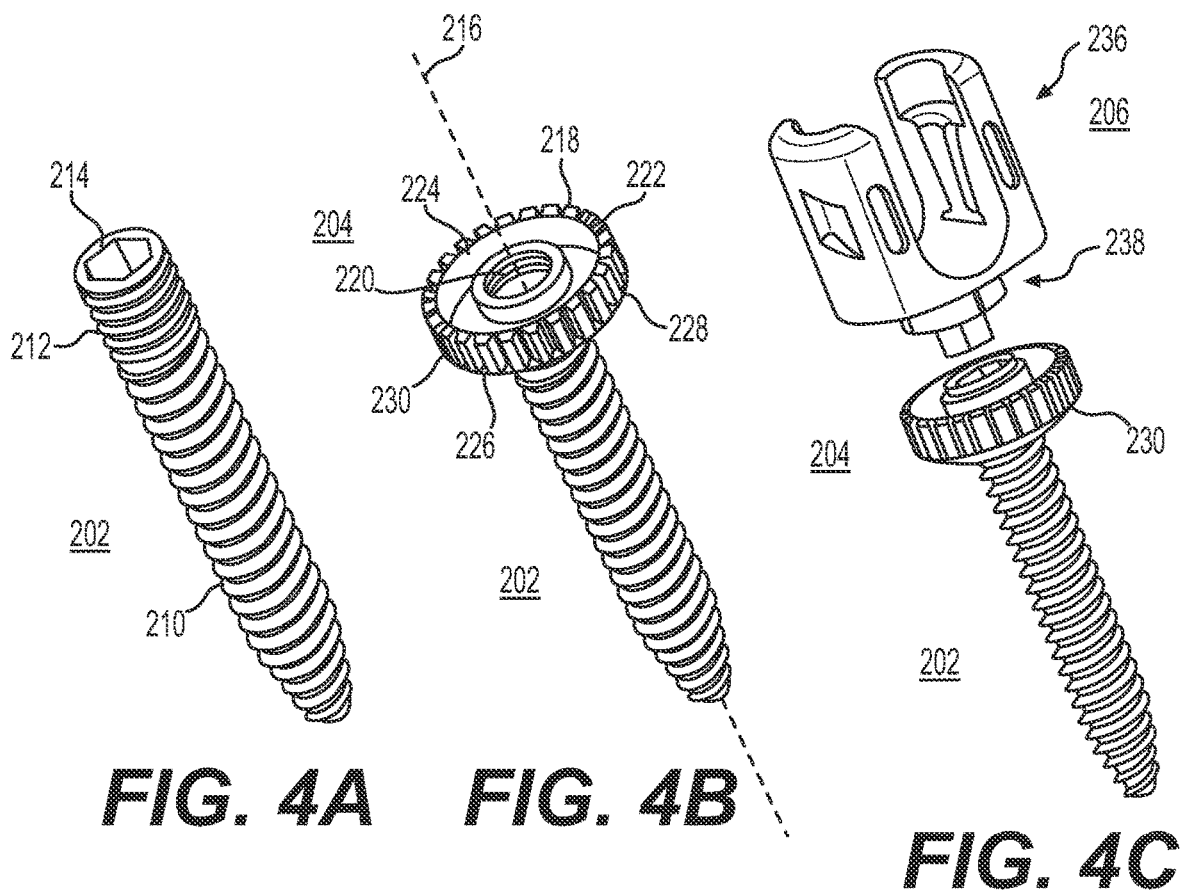
Figure 4D:
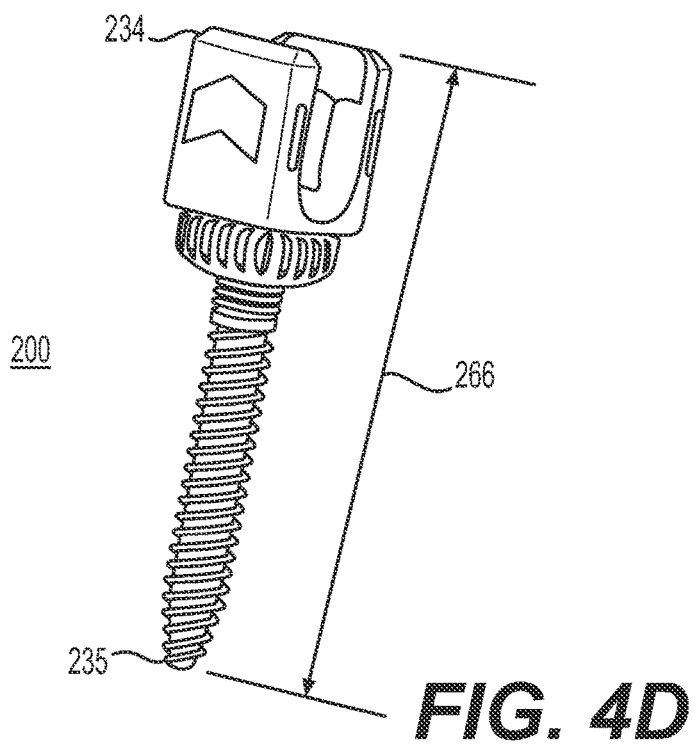
Figure 5A:
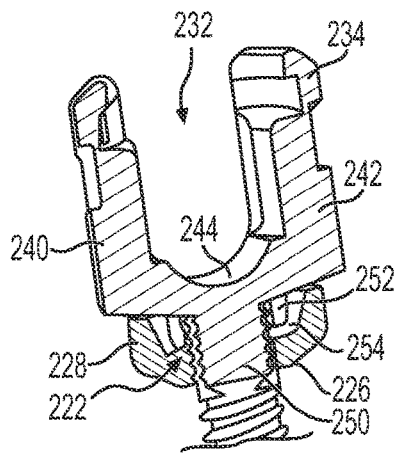
FIGS. 5A-C illustrate partial cross-section views of an assembled coupling member, elevation member, and fastener member.
Figure 5B:
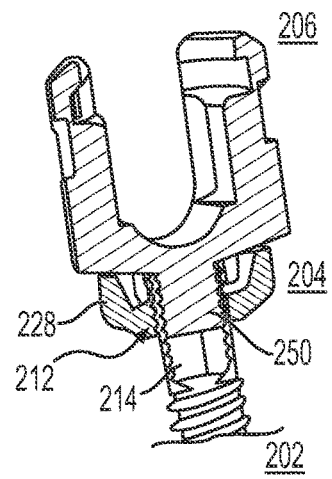
Figure 5C:
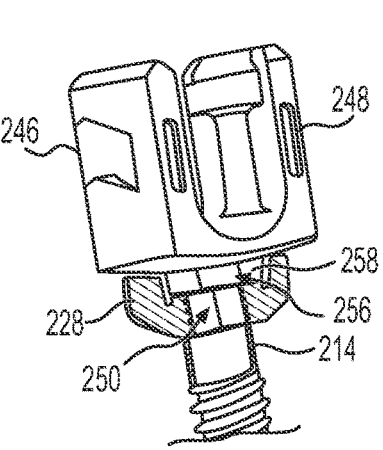

As illustrated in FIG. 4B, the elevation member 204 can be configured to be disposed on the fastener member 202. As illustrated, for example, in FIGS. 5A-C, the elevation member 204 can include a body 218. The body 218 can include a proximal face 224, a distal face 226, and a threaded hole 220 extending therethrough from the proximal face 224 to the distal face 226, as illustrated in FIGS. 4B-C. Advantageously, the threaded hole 220 can be configured to mate with the threaded head 212. The elevation member 204 can further include a first connector member 222, as illustrated in FIGS. 5A-B. The first connector member 222 can be configured to receive and/or couple to at least a portion of the coupling member 206, as described further herein. In some embodiments, the first connector member 222 can be a receptacle on the proximal face 224 of the elevation member 204. For example, in one embodiment, the first connector member 222 may be an indentation, recess, channel, or groove on the proximal face 224 of the elevation member 204. In another example, the first connector member 222 can be a circular channel surrounding the threaded hole 220, as illustrated in FIGS. 5A-C. In other embodiments, the first connector member 222 can include a plurality of grooves surrounding the threaded hole 220. In yet other embodiments, the first connector member 222 can include a protrusion, phalange, or lip. In these embodiments, the first connector member 222 can couple to at least a portion of the coupling member 206 by being received in at least a portion of the coupling member 206.

The elevation member 204 can include an outer surface 228, as illustrated in FIGS. 5A-C. The outer surface 228 can be configured to couple with a tool, such as a driver, wrench, or other implement that can apply torque to the elevation member 204. As depicted in FIGS. 4B-C, in some embodiments the elevation member 204 can be a gear member. In these embodiments, the outer surface 228 of the elevation member 204 can include a plurality of protrusions, such as teeth 230. Those skilled in the art may appreciate that the teeth 230 may be configured to mesh with the teeth of another gear member that may be mounted on a driver, for example. The gear teeth may have any configuration as known in the art. For example, the elevation member 204 can be a spur gear, a straight-cut gear, a helical gear, or a bevel gear. In some embodiments, the teeth 230 may be aligned parallel to a longitudinal axis 216.

Advantageously, the elevation member 204 can also be configured to adjust a length 266 of the spinal stabilization system 200 (e.g., from a proximal end 234 of the coupling member 206 to a distal tip 235 of the fastener member 202). In some embodiments, the elevation member 204 can be configured to rotate about the axis 216 of the spinal stabilization system 200. In other embodiments, the fastener member 202 and/or the locking member 208 may also be configured to rotate about the axis 216.

The coupling member 206 may be configured to couple the fastener member 202 to a rod. As illustrated, for example, in FIGS. 4C, the coupling member 206 can include an upper portion 236 and a lower portion 238. The upper portion 236 may be configured to receive a rod. For example, the upper portion 236 of the coupling member 206 may include two arms 240, 242 defining a rod-receiving channel 232, as illustrated in FIGS. 5A-C. The upper portion 236 can also include a seat 244 configured to contact the rod. Upon insertion and reduction, the rod may rest upon the seat 244. The shape of the seat 244 can be configured to accommodate the shape of the rod, and can be, for example, rounded, U-shaped, or partially cylindrical. The upper portion 236 of the coupling member 206 may also include a proximal end 234 configured to engage the locking member 208. For example, in some embodiments, the proximal end 234 can include interior threading. In other embodiments, the proximal end 234 can include, for example, a groove and/or a cam surface. The upper portion 236 can optionally also include one or more tool-receiving recesses 246, 248, as illustrated in FIGS. 5A-C.

At least a section of the lower portion 238 of the coupling member 206 may be configured to engage the fastener member 202. As illustrated in FIGS. 5A-C, the lower portion 238 can include a stem 250. The stem 250 can be configured to be received, and/or keyed (e.g., wedged or fastened) in the socket 214 of the fastener member 202. In these embodiments, the shape of the stem 250 and socket 214 can prevent the coupling member 206 and fastener member 202 from rotating relative to one another. The stem 250 can take on a variety of shapes, such as a rectangle, cross, star, triangle, square, hexagon, or pentagon, to fit into and couple with the socket 214. In some embodiments, at least a section of the stem 250 can have a hexagonal lateral cross-section, as illustrated in FIG. 5C. In other embodiments, the stem 250 and the socket 214 can both include at least a section having a hexagonal lateral cross section.

At least a section of the lower portion 238 of the coupling member 206 may be configured to engage the elevation member 204. In some embodiments, the lower portion 238 can include a second connector member 252, as illustrated in FIGS. 5A-C. The second connector member 252 can be configured to mate with the first connector member 222 of the elevation member 204. For example, in embodiments where the first connector member 222 includes a receptacle, the second connector member 252 can include a protrusion which is configured to be received in the receptacle. In one embodiment, the first connector member 222 can include a channel and the second connector member 252 can include a lip 254.

In some embodiments, the second connector member 252 can be bendable or flexible to fit into the first connector member 252. The second connector member 252 can be configured to bend or flex according to a variety of means, such as by including one or more longitudinal slots 256. Similarly, in these embodiments, the second connector member 252 may comprise a plurality of segments 258 separated by the slots 256. In these embodiments, illustrated in FIGS. 5A-C, the second connector member 252 may be referred to as a slotted collar.

As described herein, a portion of the coupling member 206 (e.g., the second connector member 252) may be received in a portion of the elevation member 204 (e.g., the first connector member 222). In these embodiments, the coupling member 206 can include a protrusion and the elevation member 204 can include a receptacle. However, those skilled in the art may appreciate that in other embodiments, a portion of the elevation member 204 (e.g., the first connector member 222) may be received in a portion of coupling member 206 (e.g., the second connector member 252). In these embodiments, the elevation member 204 may include a protrusion and the coupling member 206 may include a receptacle. Accordingly, any of the protrusions and receptacles described herein may be applied to either the elevation member 204 or the coupling member 206.

As illustrated in FIG. 6F, the spinal stabilization system 200 can also include a locking member 208. The locking member 208 can be configured to engage the upper portion 236 of the coupling member 206. In some embodiments, the locking member 208 may be configured to mate with the proximal end 234 of the upper portion 236 of the coupling member 206. In embodiments where the proximal end 234 includes internal threading, the locking member 208 can include external threading. For example, in these embodiments, the locking member 208 can include a set screw. In other embodiments, the locking member 208 can include a cam lock.

Embodiments herein are also directed to methods of installing the spinal stabilization system 200. The method may include providing the spinal stabilization system 200, which may or may not be at least partially assembled prior to installation. In some embodiments, the spinal stabilization system 200 may be assembled in situ (e.g., at the location where the system will be installed, such as a vertebral area of a patient) as a part of the installation process. In these embodiments, the fastener member 202 may first be installed. The fastener member 202 may be installed, for example, in any appropriate bone, such as a vertebra, and at any appropriate location thereon, as determined by those skilled in the art. In embodiments where the fastener member 202 is a pedicle screw, the fastener member 202 may be installed in (e.g., screwed or threaded into) the pedicle of a vertebra. The fastener member 202 may be installed using methods known to those skilled in the art. For example, in some embodiments, a passageway may be drilled and the fastener member 202 may be installed through a sheath, tube, or sleeve, and/or over a guide wire.

After the fastener member 202 is installed, the elevation member 204 may be coupled with the fastener member 202. In embodiments where the elevation member 204 includes a through bore with internal threading and the fastener member 202 includes a threaded head 212, the elevation member 204 may be coupled with the fastener member 202 by threading the elevation member 204 onto the threaded head 212.

The coupling member 206 may then be coupled with the fastener member 202 and the elevation member 204. In embodiments where the coupling member 206 includes a stem 250 and the head 212 of the fastener member 202 includes socket 214, the step of coupling the coupling member 206 with the fastener member 202 may include inserting the stem 250 into the socket 214, as illustrated in FIGS. 5A-C. The step of coupling the coupling member 206 with the elevation member 204 may include mating the first and second connector members 222, 252. In embodiments where second connector member 252 of the coupling member 206 includes a protrusion and the first connector member 222 of the elevation member 204 includes a receptacle, this step may include applying a distal (e.g., downward) force by pushing, sliding, snapping, and/or clicking the coupling member 206 onto the elevation member 204 so that the protrusion of the second connector member 252 is received within the receptacle of the first connector member 222. In one example where the first connector member 222 of the elevation member 204 includes a channel and the second connector member 252 of the coupling member 206 includes a slotted collar with a lip 254, this step may include inserting the lip 254 into the channel, for example, by pushing or snapping the slotted collar into the channel.

In some embodiments, the spinal stabilization system 200 may be at least partially assembled prior to installation. For example, the fastener member 202 and the elevation member 204 may be coupled as illustrated in FIG. 4B and installed, and then the coupling member 206 may be coupled with the construct in situ. In another example, the fastener member 202, elevation member 204, and coupling member 206 may be assembled as illustrated in FIG. 4D and as described herein prior to being installed. One example of a fastener member 202, elevation member 204, and coupling member 206 installed in a vertebra is illustrated in FIG. 6A.

Figure 6B:
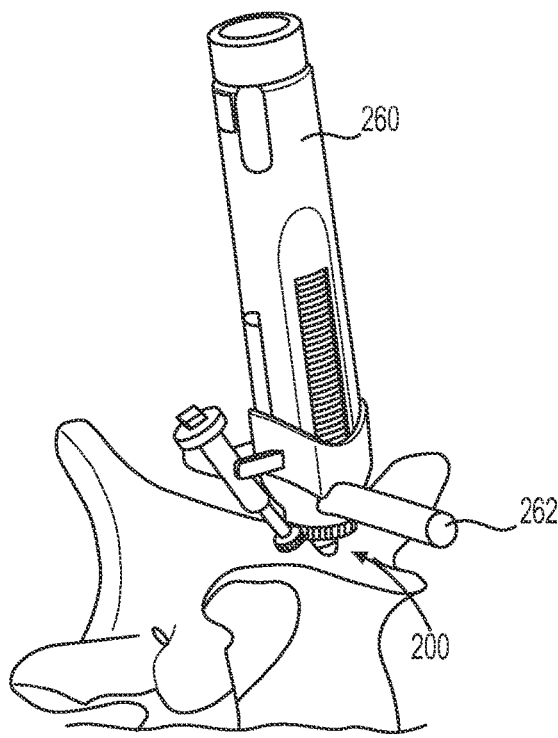

Once the fastener member 202, elevation member 204, and coupling member 206 are assembled and/or installed, a rod 262 may be inserted into the rod-receiving channel 232, as illustrated in FIG. 6B. Any rods known in the art may be used with the spinal stabilization system 200 described herein. Additional tools, such as a rod reducer 260, may also be used to insert the rod 262 into the rod-receiving channel 232, as illustrated in FIG. 6B. The rod 262 may be secured against the seat 244 in the rod-receiving channel 232 by engaging the locking member 208 with the proximal end 234 of the coupling member 206. In some embodiments, the locking member 208 may be delivered to the spinal stabilization system 200 through a cannula in the rod reducer 260. In embodiments where the locking member 208 includes a set screw and the proximal end 234 of the coupling member 206 includes an internally-threaded section, this step can include threading the set screw into the internally-threaded section. When the rod is secured in the rod-receiving channel, it may contact both the seat 244 and a distal surface of the locking member 208.

Figure 6C:
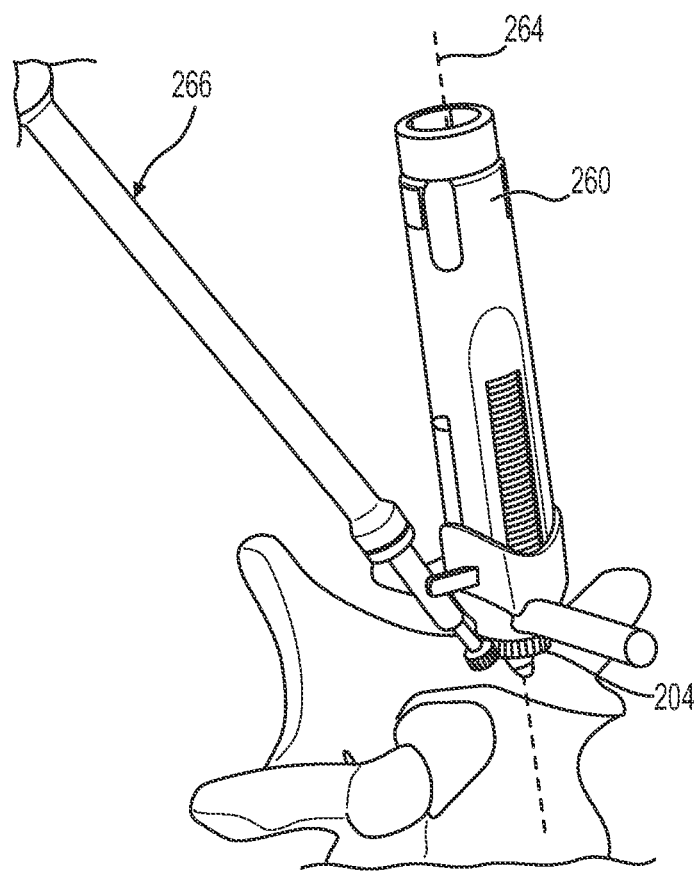
Figure 6D:
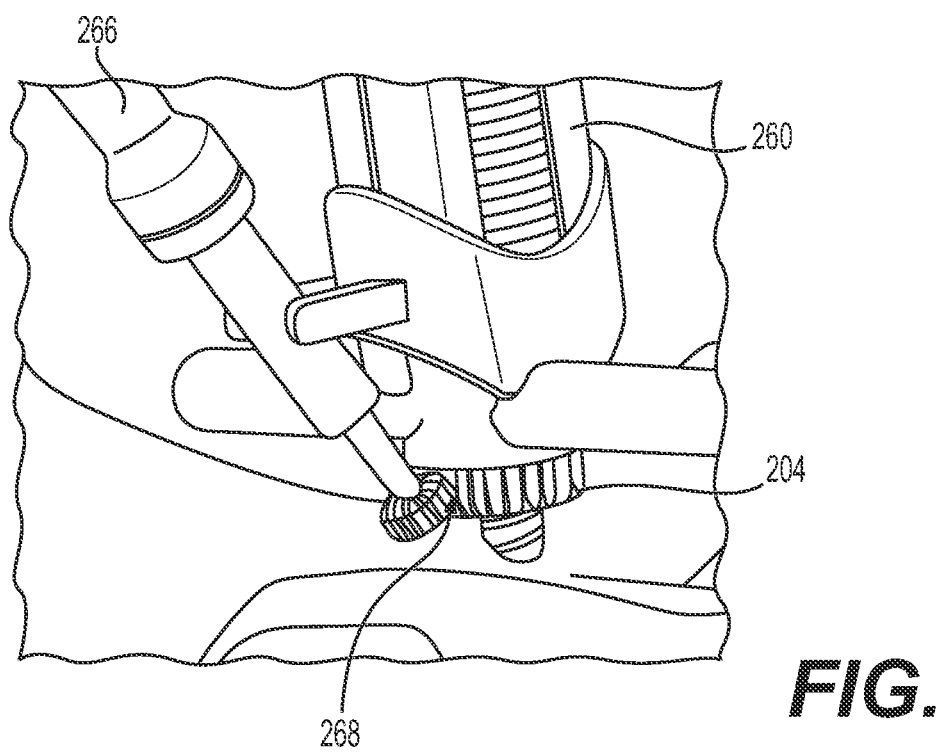
Figure 6E:
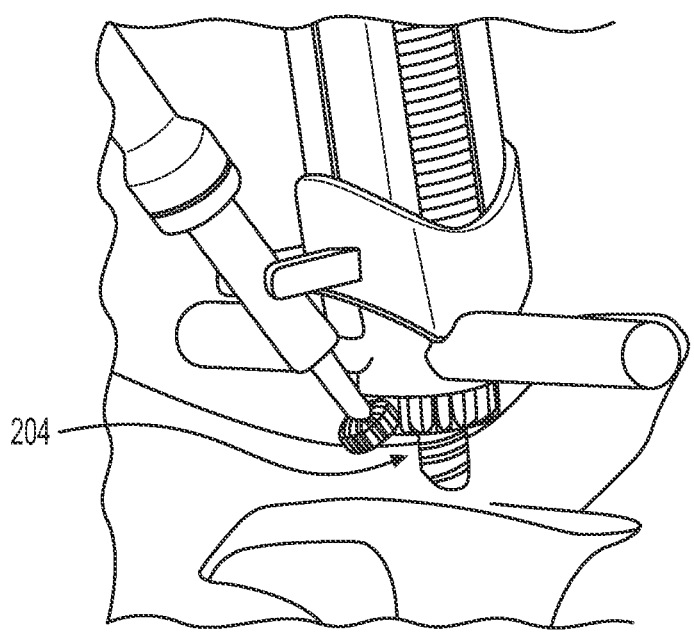
Figure 6F:
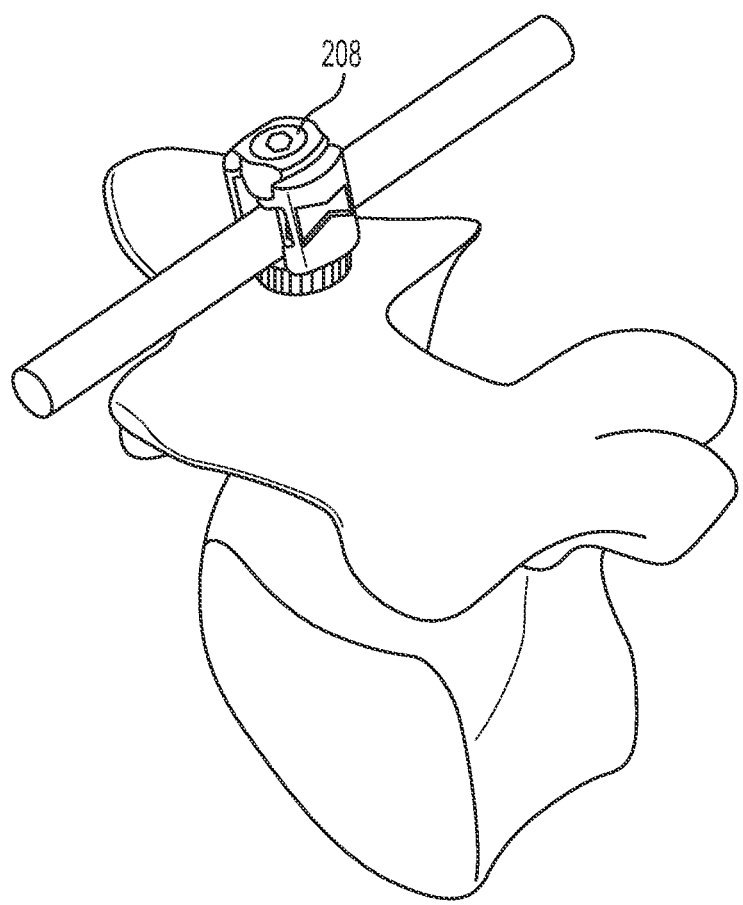

After the rod is secured in the rod-receiving channel, the position of the coupling member 206 may advantageously be adjusted along a longitudinal axis 264 of the spinal stabilization system 200, as illustrated in FIG. 6C. This may be accomplished by rotating the elevation member 204. As illustrated in FIGS. 6D-E, the elevation member 204 may be rotated by a driver 266. In embodiments where the elevation member 204 includes a gear member, the driver 266 can include a second gear 268 that is configured to mesh with the gear teeth of the elevation member 204. As further illustrated in FIGS. 6D-E, the driver 266 may be configured to couple with the rod reducer 260.

In use, because the elevation member 204 can be coupled to the coupling member 206, as the elevation member 204 is threaded in the proximal (e.g., upwards) direction, the coupling member 206 may also be pushed upwards, as illustrated in FIGS. 6D-E. Similarly, when the elevation member 204 is threaded in the distal (e.g., downwards) direction, the coupling member may also be pulled downwards. Accordingly, the length 266 of the construct (e.g., from the proximal end 234 of the coupling member 206 to the distal tip 235 of the fastener member 202) can be varied or adjusted by rotating the elevation member 204. Advantageously, the ability to provide further adjustment to the length of the construct after being secured to a rod can be useful in procedures where long rods are used in conjunction with large numbers of fastener members (e.g., in deformity procedures). In these procedures, it may be difficult to precisely align all of the rod-receiving channels prior to insertion of the rod. The present spinal stabilization system 200 may alleviate this issue by enabling fine-tuning of the longitudinal position of the coupling member 206 after the rod has been inserted and secured.

As described herein, the elevation member 204 and the coupling member 206 may engage with a monoaxial fastener member (e.g., a fastener member capable of engaging the coupling member 206 at a single angle). However, those skilled in the art may appreciate that in other embodiments, the elevation member 204 and the coupling member 206 may engage with a polyaxial fastener member (e.g., a fastener member capable of engaging the coupling member 206 at multiple angles). For example, the coupling member 206 may be modified using techniques known in the art to accommodate the polyaxial fastener members described herein, such as those used with spinal stabilization system 400. Additionally, some embodiments of the spinal stabilization system 200 may include or be combined with features of other spinal stabilization systems described herein.

Figure 7A:
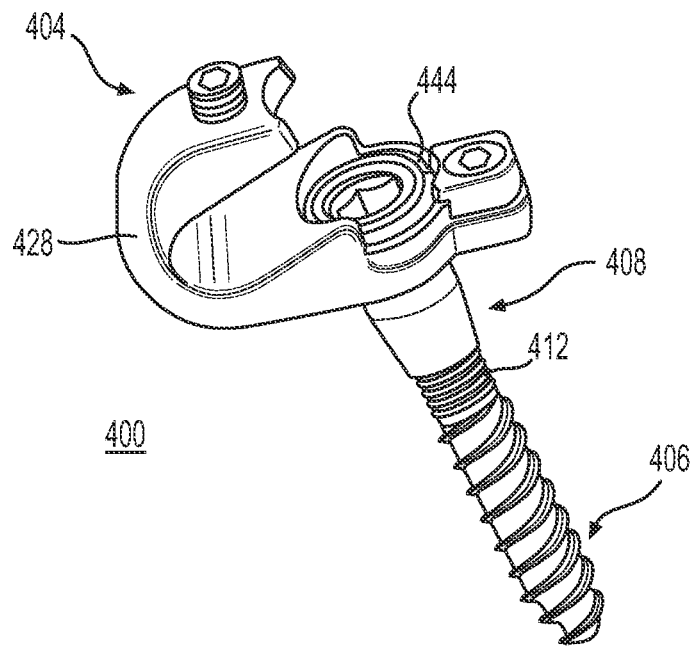
FIGS. 7A-B illustrate perspective views of one embodiment of a spinal stabilization system as disclosed herein.
Figure 7B:
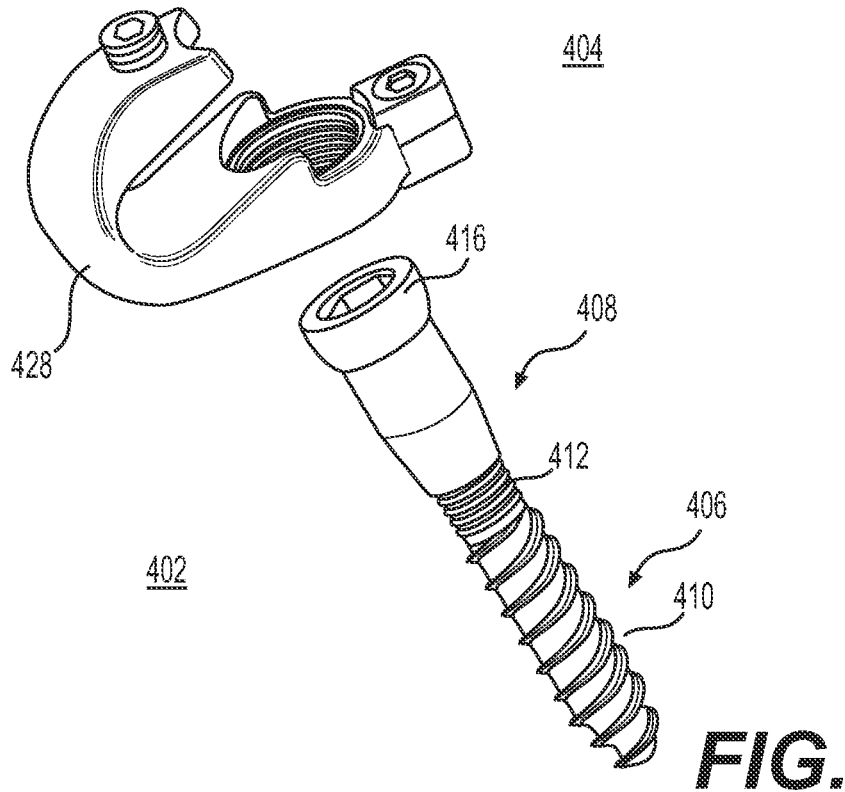
Figure 8:
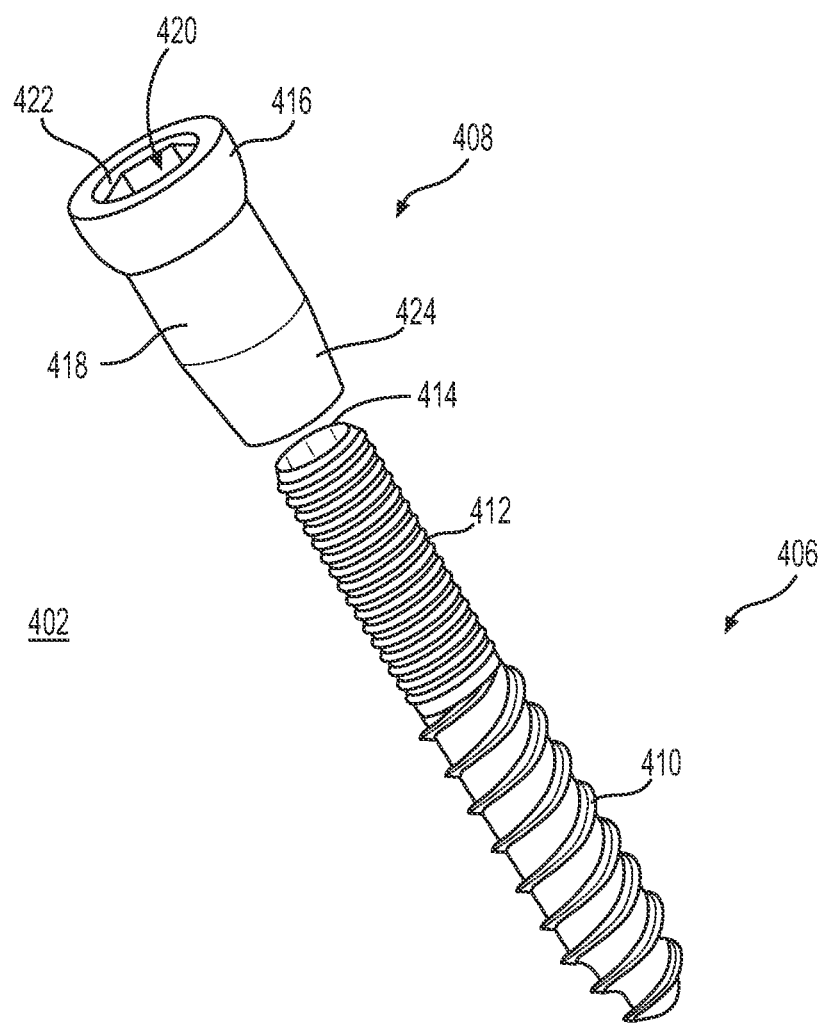
FIG. 8 illustrates an exploded view of a fastener assembly.

Turning now to FIG. 7A-12, a spinal stabilization system 400 and its components are illustrated in accordance with embodiments described herein. The spinal stabilization system 400 can include a fastener assembly 402 and a clamp assembly 404, as illustrated in FIG. 7B. The fastener assembly 402 can include a fastener member 406 and a compression member 408, as illustrated in FIG. 8. The fastener member 406 can include a threaded shank 410. The threaded shank 410 can extend longitudinally from a head 412. In some embodiments, the fastener member 406 can be monolithic. In some embodiments, the head 412 can be threaded (e.g., can include exterior and/or interior threading). The head 412 can include a cylindrical (e.g., constant diameter) outer surface. For example, in some embodiments, where the head 412 is cylindrical, it may be referred to as a post. In other embodiments where the head 412 is cylindrical and includes exterior threading, it may be referred to as a threaded post. In these embodiments, the threaded head 412 can include a constant major thread diameter and/or a constant minor thread diameter. In some embodiments, the fastener member 406 may be referred to as a posted screw. In some embodiments, the fastener member 406 may be a pedicle screw, such as a monoaxial or polyaxial screw. In some embodiments, the fastener member 406 may be a pedicle screw, such as a monoaxial or polyaxial pedicle screw. The head 412 can further include a socket 414. The socket 414 can be configured to receive a driver, such as a screwdriver or a hex key. The lateral cross-sectional shape of the socket 414 can vary to accommodate various drivers, and can be, for example, a slot, cross, star, triangle, square, hexagon, or pentagon. In some embodiments, at least a section of socket 414 can include a hexagonal lateral cross-section.

As illustrated in FIG. 8, the compression member 408 can include a head 416 and an elongate body 418. The head 416 can have a rounded outer surface (e.g., can include a spherical or spheroidal segment). The head 416 can have a lateral diameter that is greater than a lateral diameter of the elongate body 418. In some embodiments, the elongate body 418 can have a constant-diameter outer surface. In other embodiments, the elongate body 418 can include a distal portion 424, having a tapered outer surface.

The compression member 408 can also include a longitudinal bore 420 extending therethrough. A portion of the longitudinal bore (e.g., a proximal portion within the head 416) can include a socket 422. The socket 422 can be configured to receive a driver, such as a screwdriver or a hex key. The lateral cross-sectional shape of the socket 422 can vary to accommodate various drivers, and can be, for example, a slot, cross, star, triangle, square, hexagon, or pentagon. In some embodiments, at least a section of socket 422 can include a hexagonal lateral cross-section.

The socket 422 of the compression member 408 and the socket 414 of the fastener member 406 may each have a lateral (e.g., transverse) width or diameter. In some embodiments, the width of the socket 422 of the compression member 408 can be greater than the width of the socket 414 of the fastener member 406. Advantageously, in some embodiments, both sockets 414, 422 may be accessible by a driver even when the compression member 408 and fastener member 406 are engaged with each other, as described further herein.

A portion of the longitudinal bore 420 (e.g., a distal portion within the elongate body 418 and/or distal portion 424) can be configured to engage the head 412 of the fastener member 406. In some embodiments, the portion of the longitudinal bore 420 that is configured to engage the head 412 of the fastener member 406 can be configured to rotatably engage the head 412, for example, by including internal threading that is configured to mate with external threading on the head 412. In other embodiments, the compression member 408 can be configured to slideably engage the head 412 of the fastener member 406 (e.g., by including a combination of a cam member and a groove on the head 412 and the compression member 408). In embodiments where the compression member 408 is coupled to, engaged with, and/or threaded onto the fastener member 406, the fastener assembly 402 may be referred to as being assembled.

Figure 9A:
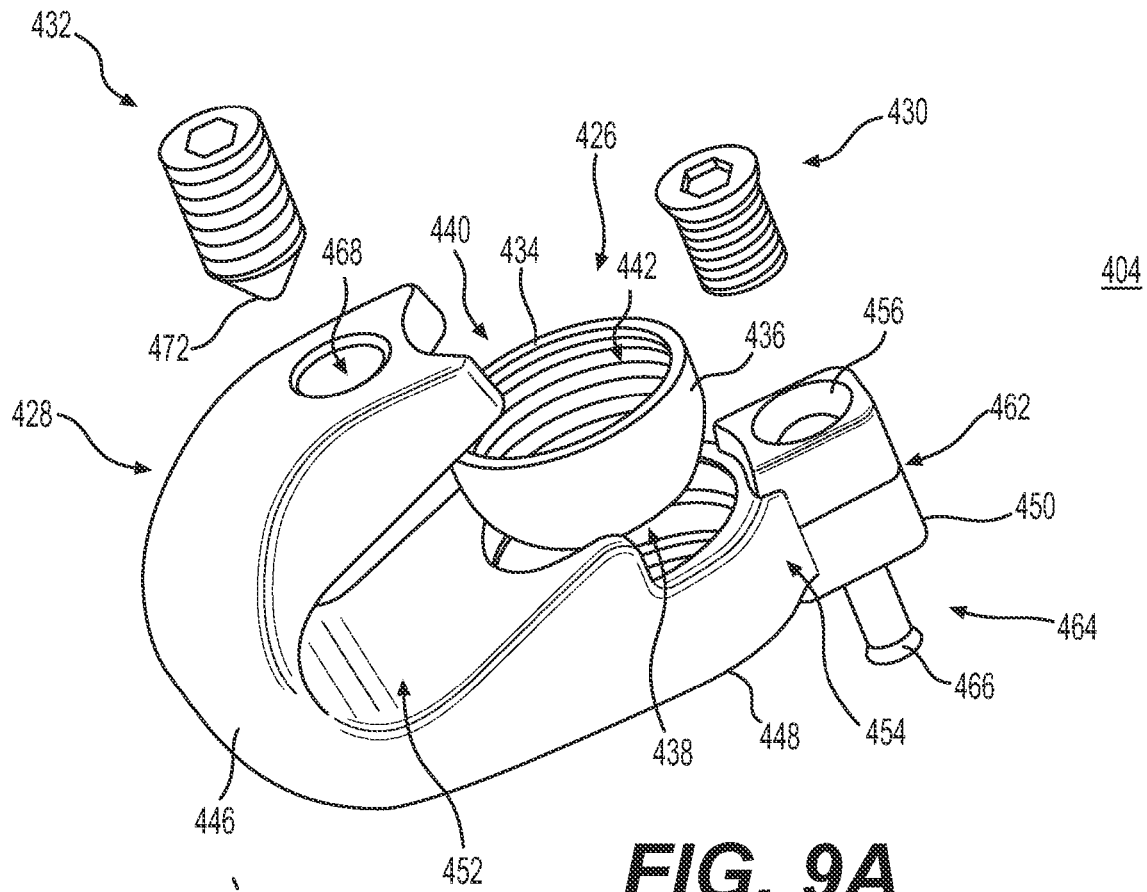
FIGS. 9A-B illustrate a perspective view and an exploded view of a clamp assembly.
Figure 9B:
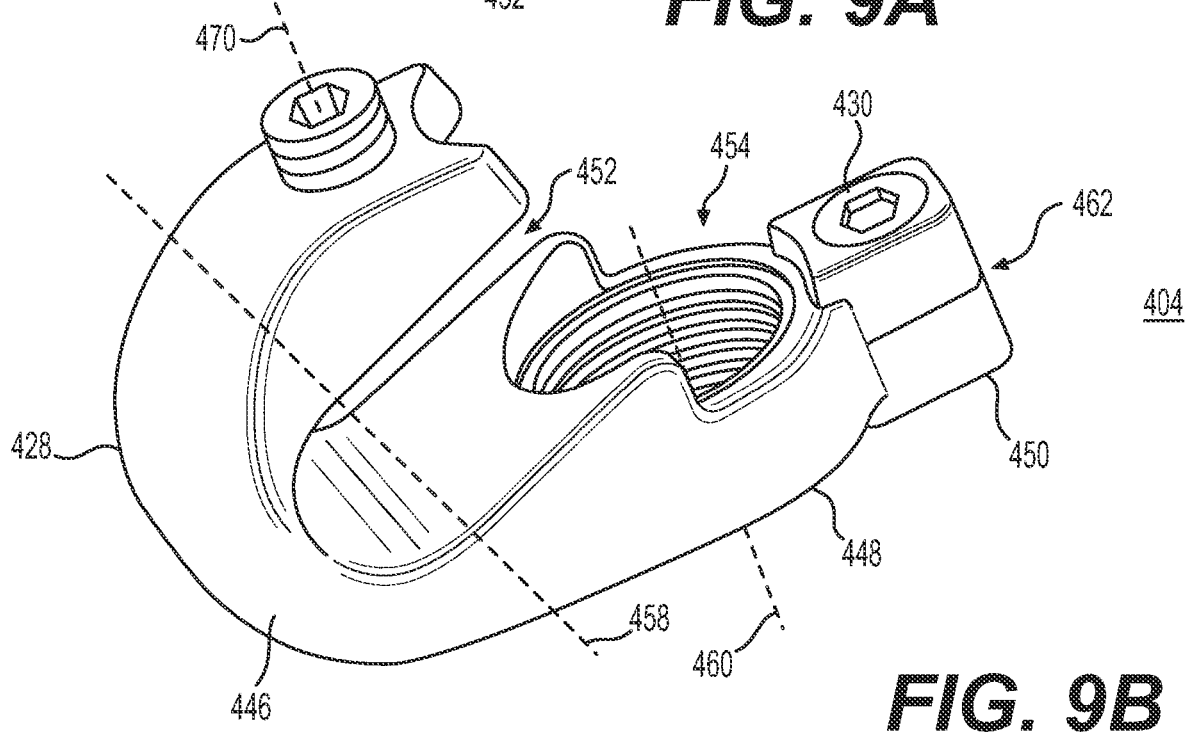

As illustrated in FIGS. 9A-B, the clamp assembly 404 can include a clamp member 426, a coupling member 428, a first locking member 430, and a second locking member 432. The clamp member 426 may include an inner surface 434 and an outer surface 436. The inner surface 434 may be configured to receive the head 416 of the compression member 408 thereon. In some embodiments where the head 416 is curved or rounded, the inner surface 434 may also be curved or rounded, optionally to match a degree of curvature of the head 416. The outer surface 436 may be configured to engage the coupling member 428. The outer surface 436 may also be curved or rounded, optionally to match a degree curvature of a surface of the coupling member 428. In some embodiments, the outer surface 436 can include an engagement feature (e.g., a groove or projection) that can mate with a corresponding feature on the coupling member 428.

The clamp member 426 may also include a chamber 442 that extends from a proximal opening 440 to a distal opening 438. The proximal opening 440 may be sized and/or configured to receive the fastener assembly 402 therethrough. In some embodiments, the proximal opening 440 may have a diameter that is greater than or equal to the diameter of the head 416. The distal opening 438 may be configured to receive the fastener member 406 and/or elongate body 418 of the compression member 408 therethrough. The distal opening 438 may have a diameter that is greater than a diameter of the elongate body 418 and less than a diameter of the head 416. Accordingly, the head 416 may rest within the chamber 442 and/or on the inner surface 434 of the clamp member 426 without passing through the distal opening 438.

The clamp member 426 may be expandable and/or contractible. In some embodiments, the diameter of the clamp member 426 may reversibly increase or decrease upon the application or release of an external force. Consequently, the volume of the chamber 442 may also be configured to increase or decrease. In some embodiments, the clamp member 426 may be configured to contract (e.g., compress, clamp, or constrict) around the head 416 of the compression member 408. In some embodiments, the clamp member 426 can include a slot 444, as illustrated in FIG. 7A. In some embodiments, the slot 444 can extend partially from the proximal opening 440 to the distal opening 438, or vice versa. In other embodiments, the slot 444 can extend completely from the proximal opening 440 to the distal opening 438. In other embodiments, the clamp member 426 can include a plurality (e.g., two, three, four, or more) of slots. The shape of the slot 444 may vary. In some embodiments, the slot 444 may be a straight line. In other embodiments, the slot 444 may include a plurality of straight lines intersecting at one or more angles (e.g., a zigzag shape). In yet other embodiments, the slot 444 may include a curved line.

In other embodiments, the clamp member 426 can include a plurality of separate clamp elements or pieces. In some embodiments the clamp member 426 can be made of two clamp elements. In other embodiments, the clamp member 426 can include two, three, four, or more clamp elements. Each clamp element can include a curved or rounded inner and outer surface, as discussed herein with respect to the singular clamp member 426. The clamp elements may be equally sized and shaped.

In some embodiments, the inner surface 434 of the clamp member 426 can include a roughened surface. As illustrated in FIG. 9A, in some embodiments, the inner surface 434 can include threading. In other embodiments, the roughened surface can include one or more features such as threads, grooves, bumps, ridges, knurling, and knobs.

As illustrated in FIGS. 9A-B, the coupling member 428 can include a rod-receiving portion 446, a fastener-receiving portion 448, and a locking portion 450. The rod-receiving portion 446 can include a channel 452. The channel 452 may include a longitudinal axis 458 and can be configured to receive a rod. The fastener-receiving portion 448 can include an aperture 454 having a longitudinal axis 460. As illustrated in FIG. 9A, the channel 452 may be at least partially laterally offset from the aperture 454. Additionally, as illustrated in FIG. 9A, the longitudinal axes 458, 460 may not intersect. In some embodiments, the longitudinal axes 458, 460 may be orthogonal or transverse to each other.

As illustrated in FIG. 9A, the locking portion can include a first locking receptacle 456. The first locking receptacle 456 may be at least partially laterally offset from the aperture 454. In some embodiments, the first locking receptacle 456 can include a threaded interior surface. The first locking receptacle 456 can be configured to receive the first locking member 430. In use, the first locking member 430 may be configured to lock or secure the fastener assembly 402 at a particular angle relative to the clamp assembly 404. Thus, in some embodiments, the first locking member 430 may be referred to as a fastener-locking member. The first locking member 430 can include interior and/or exterior threading. As illustrated in FIG. 9A, the first locking member 430 may be a screw, such as a set screw. In some embodiments, the first locking member 430 can be configured to engage a securing member 464, such as a nut. The securing member 464 may have an enlarged head 466. The securing member 464 may also include exterior threading configured to engage the interior threading of the first locking member 430, and may be threaded into the first locking member 430. In some embodiments, the interior and exterior threading on the first locking member 430 may be oriented in opposite directions. Thus, in use, the securing member 464 can prevent or reduce the likelihood of the first locking member 430 from unthreading or backing out of the first locking receptacle 456.

As illustrated in FIGS. 9A-B, the coupling member 428 can include a transverse slot 462. The transverse slot 462 can extend at least partially through the fastener-receiving portion 448 (e.g., at least partially across the first locking receptacle 456). The transverse slot 462 can also extend at least partially through the locking portion 450 (e.g., at least partially across the aperture 454). In some embodiments, the transverse slot 462 may render the aperture 454 the first locking receptacle 456 in fluid communication with each other (e.g., the aperture 454 and the first locking receptacle 456 may be connected, either directly or indirectly via a conduit or passageway).

As illustrated in FIG. 9A, the rod-receiving portion 446 can include a second locking receptacle 468. The second locking receptacle 468 can include a longitudinal axis 470. The longitudinal axis 470 of the second locking receptacle 468 can be orthogonal to the longitudinal axis 458 of the channel 452. In some embodiments, the longitudinal axis 470 of the second locking receptacle 468 can intersect the longitudinal axis of the channel 452. In some embodiments, the second locking receptacle 468 and the channel 452 may be in fluid communication.

The second locking receptacle 468 may be configured to receive and/or engage the second locking member 432 therein. In use, the second locking member 432 may be configured to lock or secure a rod within the channel 452.

Thus, in some embodiments, the second locking member 432 may be referred to as a rod-locking member. In some embodiments, the second locking receptacle 468 can include interior threading. In these embodiments, the second locking member 432 can include exterior threading, and can be, for example, a set screw. As illustrated in FIG. 9A, the second locking member 432 can include a distal tip 472 configured to engage a rod, for example, in a friction or interference fit. The shape of the distal tip 472 can vary. In some embodiments, the distal tip 472 can be conical. In other embodiments, the distal tip 472 can be pointed.

Those skilled in the art may appreciate that other variations on the clamp assembly may be used in combination with the fastener assembly 402 as described herein. For example, in other embodiments, the coupling member 428 may be configured such that the rod-receiving channel is not laterally offset from the fastener assembly-receiving aperture, such as with tulip-style coupling or housing members. In these embodiments, the rod and the fastener assembly may be locked or secured at the same time using a single locking member.

Additionally, some embodiments of the spinal stabilization system 400 may include features of other spinal stabilization systems described herein. As one example, in some embodiments, the fastener assembly 402 can include an elevation member, such as elevation member 204 or other gear member, that can be disposed on or adjacent to the compression member 408. In these embodiments, the overall length of the assembly may be adjusted by rotating the elevation member, as described herein with respect to the spinal stabilization assembly 200. The elevation member 204 may thus be configured to translate the compression member 408 along a longitudinal axis. Furthermore, the coupling element 206 may be modified using techniques known in the art to accommodate a polyaxial fastener, such as the polyaxial fastener assembly 402. For example, the coupling element 206 may be modified to include a bore extending therethrough, the bore having a rounded interior surface that is configured to receive the head 416 of the compression member 408 thereon.

Embodiments herein are also directed to methods of installing the spinal stabilization system 400. In some embodiments, methods can include providing an assembled spinal stabilization system 400. One example of an assembled spinal stabilization system 400 is illustrated in FIG. 7A. In these embodiments, the fastener assembly 402 may be assembled by coupling the compression member 408 and fastener member 406, as described herein. The clamp member 426 may be inserted into or disposed within the aperture 454 of the coupling member 428. As described herein, in some embodiments the clamp member 426 can include a projection that is configured to be received in a groove within the aperture 454. In these embodiments, the clamp member 426 may be snapped or clicked into engagement with the aperture 454 of the coupling member 428. The head 416 of the assembled fastener assembly 402 may be disposed within the chamber 442 of the clamp member 426, with the elongate body 418 disposed in the distal opening 438. In some embodiments, this configuration may be achieved by inserting the assembled fastener assembly 402, with the fastener member 406 as the leading end, into the chamber 442 from the proximal opening 440 towards the distal opening 438 of the clamp member 426 (e.g., may be top-loading). In other embodiments, this configuration can be achieved by inserting the assembled fastener assembly 402, with the compression member 408 as the leading end, into the chamber 442 from the distal opening 438 towards the proximal opening of the clamp member 426 (e.g., may be bottom-loading).

In some embodiments, the first locking member 430 may be threaded into the first locking receptacle 456, and the securing member 464 may be threaded into the first locking member 430. The first locking member 430 and the securing member 464 may be loosely threaded to allow the head 416 to pivot within the clamp member 426. In some embodiments, the second locking member 432 may be threaded into the second locking receptacle 468. The second locking member 432 may also be loosely threaded so as to minimize interference with the insertion of a rod into the channel 452. Those skilled in the art may appreciate that in other embodiments, the first locking member 430, securing member 464, and/or second locking member 432 may not form a part of the spinal stabilization system 400 as assembled prior to installation. Rather, they may be added to the system when the head 416 is secured within the clamp member 426 and/or when the rod is secured within the channel 452, as described further herein.

Figure 10A:
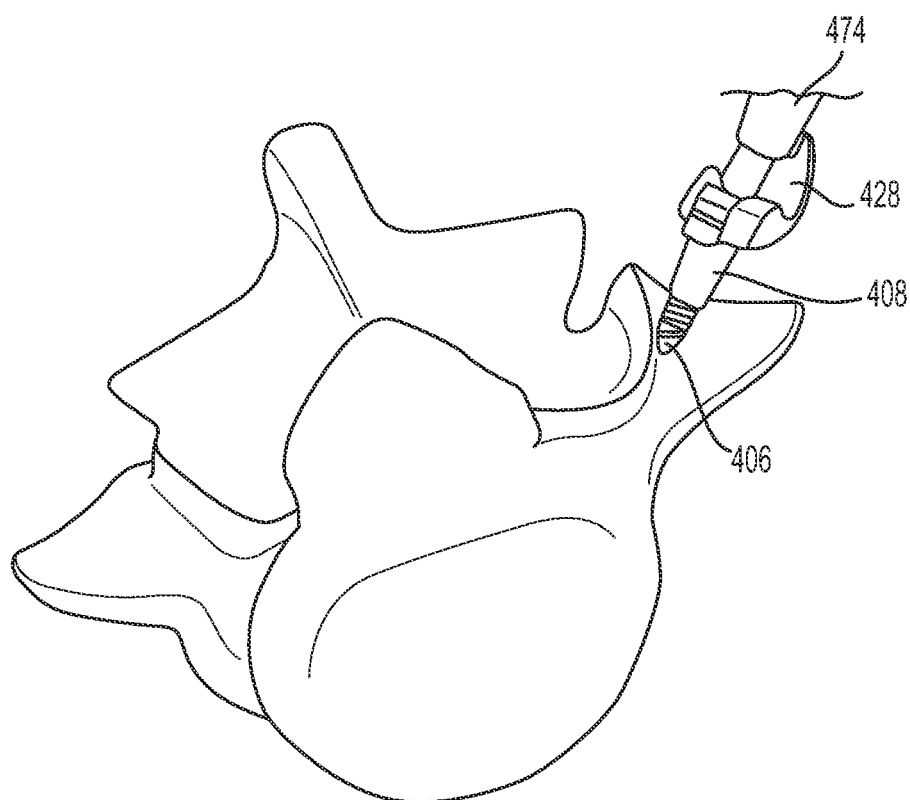
FIGS. 10A-B illustrate the engagement of a spinal stabilization system with a driver.
Figure 10B:
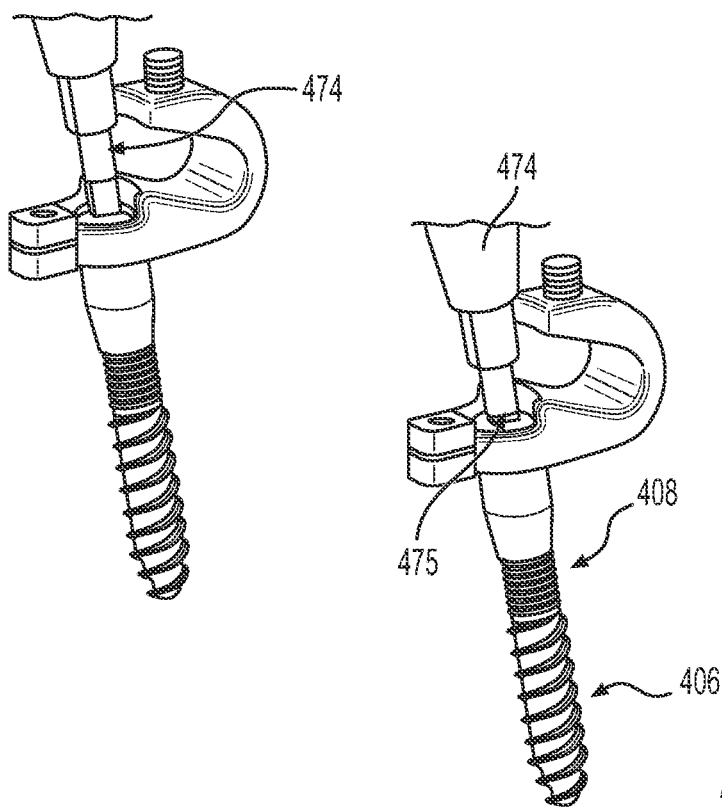

Once the spinal stabilization system 400 is assembled, or an assembled system is provided, the fastener member 406 may be inserted into a bone. As illustrated in FIG. 10A, the fastener member 406 may be inserted into a pedicle; however, in other embodiments the fastener member 406 may be inserted into another part of a vertebra or in a different bone. The fastener member 406 may be inserted into a bone according to methods known to those skilled in the art. In one example, prior to installing the fastener member 406, the installation site may be prepared by creating (e.g., drilling) a hole through which the fastener member 406 may pass. For example, a hole may be drilled, and the fastener member 406 may be driven or threaded into the hole. As illustrated in FIG. 10B, the socket 414 of the fastener member 406 may receive a driver 474, which can transfer torque to the fastener member 406. Advantageously, because the socket 422 of the compression member 408 may be larger (e.g., may have a greater diameter) than the socket 414 of the fastener member 406, the fastener member 406 can be accessed by a driver even after the fastener assembly 402 is assembled. Additionally, this feature can allow the fastener member 406 and the compression member 408 to be actuated separately.

Figure 11C:
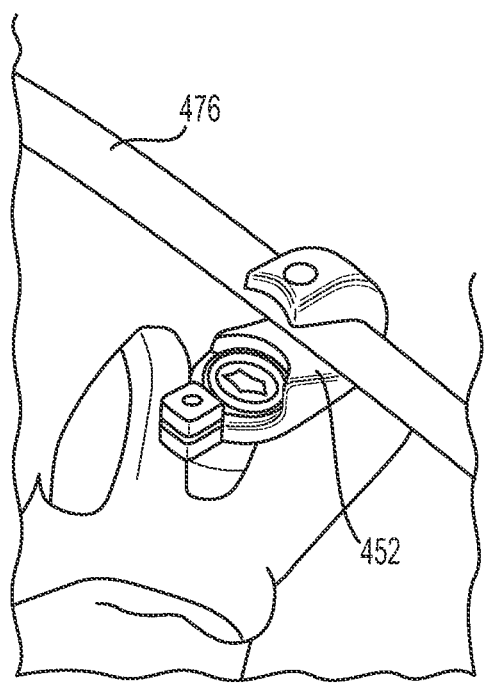
Figure 11C:
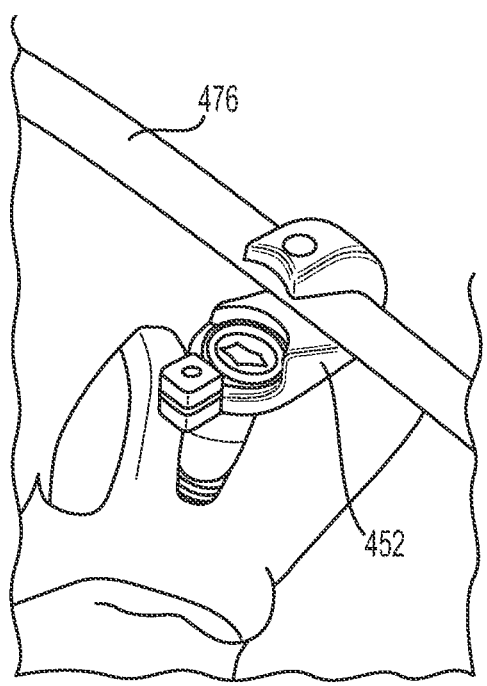
Figure 11C:
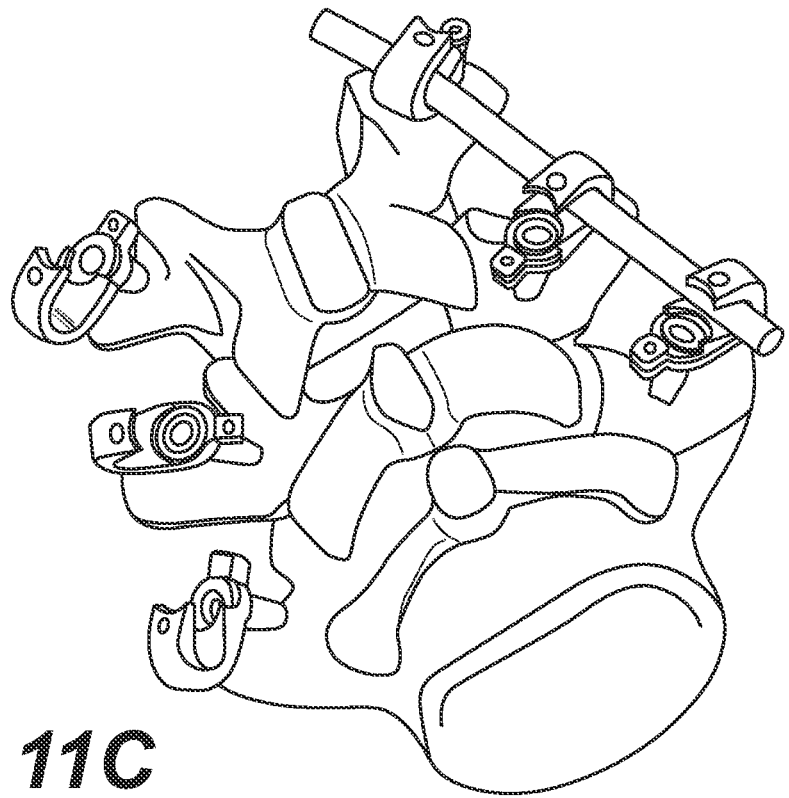

A rod 476 may then be inserted into the channel 452, as illustrated in FIGS. 11A-B. Any rods known in the art may be used with the spinal stabilization system 400, such as straight, curved, hard, soft, deformable, and/or expandable rods. Furthermore, the rod may be inserted using methods and/or devices known to those skilled in the art. For example, a rod reducer, fork, and/or persuader may be used to insert the rod 476 into the channel 452. Additionally, as illustrated in FIG. 11C, multiple spinal stabilization systems 400 may be installed, for example, in a spine. In these embodiments, the step of inserting the rod can include inserting the rod 476 into the channel 452 of each spinal stabilization system 400.

Figure 12:
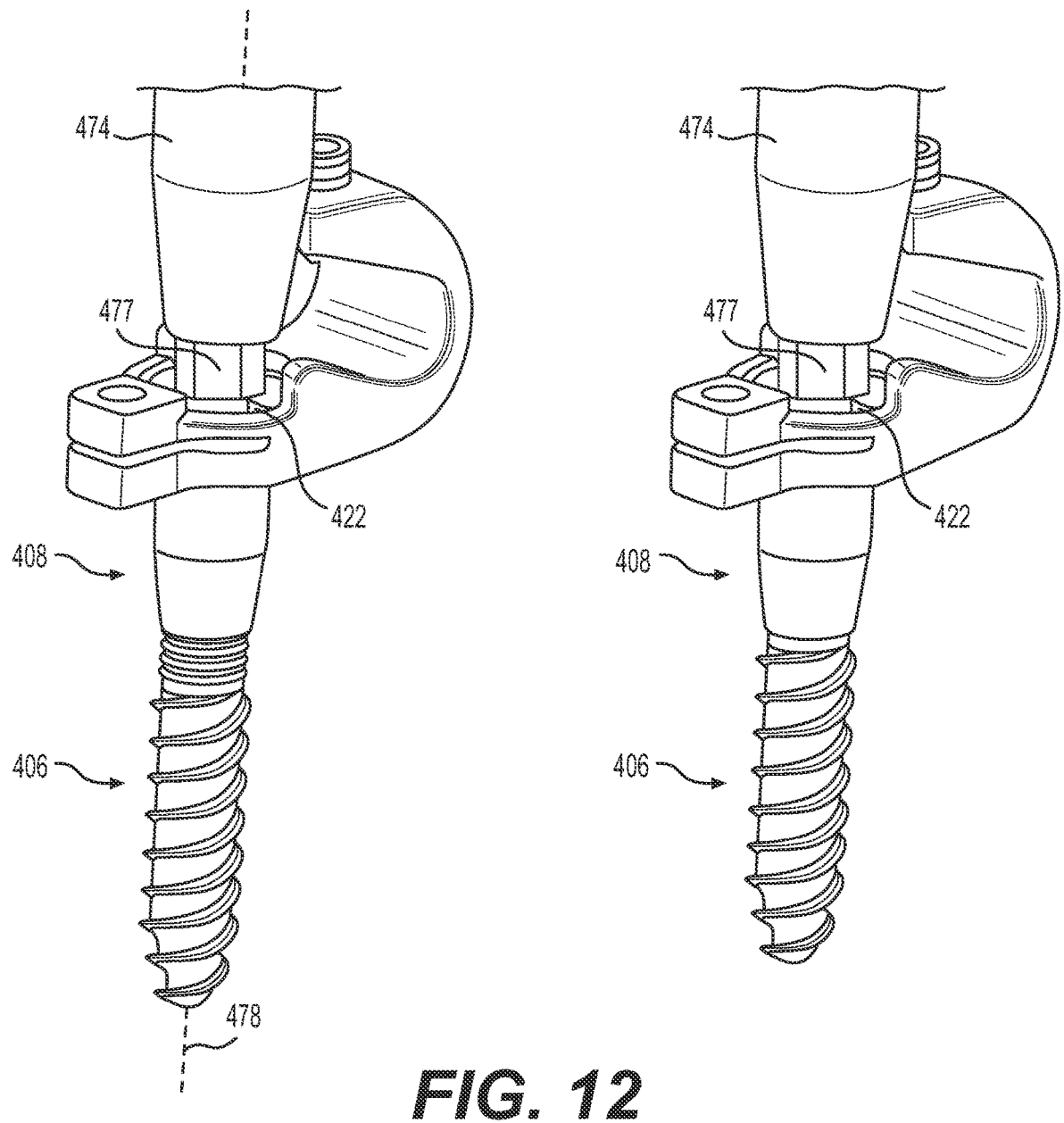
FIG. 12 illustrates the translation of a compression member as described herein.

Advantageously, the position (e.g., length and/or angle) of the fastener assembly 402 may be adjusted after the rod 476 has been inserted in the channel 452. The length may be adjusted by adjusting a position of the compression member 408 along a longitudinal axis 478, as illustrated in FIG. 12. The driver 474 can engage the socket 422 to translate the compression member 408 up and down along the head 412 of the fastener member 406, thereby modifying the overall length (e.g., height) of the fastener assembly 402. Advantageously, driver 474 can include an inner drive shaft 475 and an outer drive shaft 477, as illustrated in FIGS. 10B and 12. Accordingly, driver 474 can be used to drive the fastener member 406 into a bone as well as to adjust the length of the fastener assembly 402. However, those skilled in the art may appreciate that other drivers may also be used.

Because the compression member 408 may be engaged with the clamp assembly 404, translation or adjustment of the compression member 408 can also additionally result in translation or adjustment of the clamp assembly 404. Advantageously, the position of the spinal stabilization system 400 can be adjusted without having to remove and/or reshape the rod 476. In procedures utilizing a large number of spinal stabilization systems and/or a long rod, such as deformity procedures, this capability can potentially save time and reduce risk to a patient.

As described herein, the fastener assembly 402 may be configured to engage the clamp assembly 404 at multiple angles. The angle of the fastener assembly 402 relative to the clamp assembly 404 may be adjusted by pivoting the head 416 of the fastener assembly 402 within the chamber 442 of the clamp member 426, and/or by pivoting the clamp member 426 (and, consequently, the coupling member 428) about the head 416 of the fastener assembly 402. The angle of the fastener assembly 402 relative to the clamp assembly 404 may then be secured by compressing the clamp member 426 around the head 416. This may be accomplished, for example, by threading the first locking member 430 into the first locking receptacle 456 and onto the securing member 464. As the first locking member 430 and the securing member 464 are brought closer together, the slot 462 may be squeezed or compressed. In turn, the aperture 454 may also be compressed, thereby also compressing the clamp member 426.

After the rod 476 has been inserted into the channel 452, the second locking member 432 may be inserted (e.g., threaded) into the second locking receptacle 468 to secure the rod in the channel 452. Those skilled in the art may appreciate that the second locking member 432 can pass through the second locking receptacle 468 to the channel 452. When a rod is in the channel 452, the second locking member 432 can apply friction to the rod, thereby securing it within the channel 452. Those skilled in the art may appreciate that the steps of adjusting the length of the fastener assembly 402, adjusting and securing the angle of the fastener assembly 402, and securing the rod 476 in the channel 452 may occur in any order. In some embodiments, the rod 476 can be locked in the channel 452 either before or after any or all of the steps of adjusting the length of the fastener assembly 402, adjusting the angle of the fastener assembly 402, and securing the angle of the fastener assembly 402.

In some embodiments, all or a portion of the spinal stabilization system 400 can be assembled as part of the installation process. For example, in one embodiment, all of the components can be pre-assembled except for the second locking member 432, which can be added to the system after the rod 476 is placed in the channel 452. In other embodiments, the fastener assembly 402, either assembled or unassembled, may be inserted into a bone prior to coupling with the clamp assembly 404. After coupling of the fastener assembly 402 with the clamp assembly 404, the remaining steps for installing the spinal stabilization system 400 as described herein may be followed.

Figure 13:
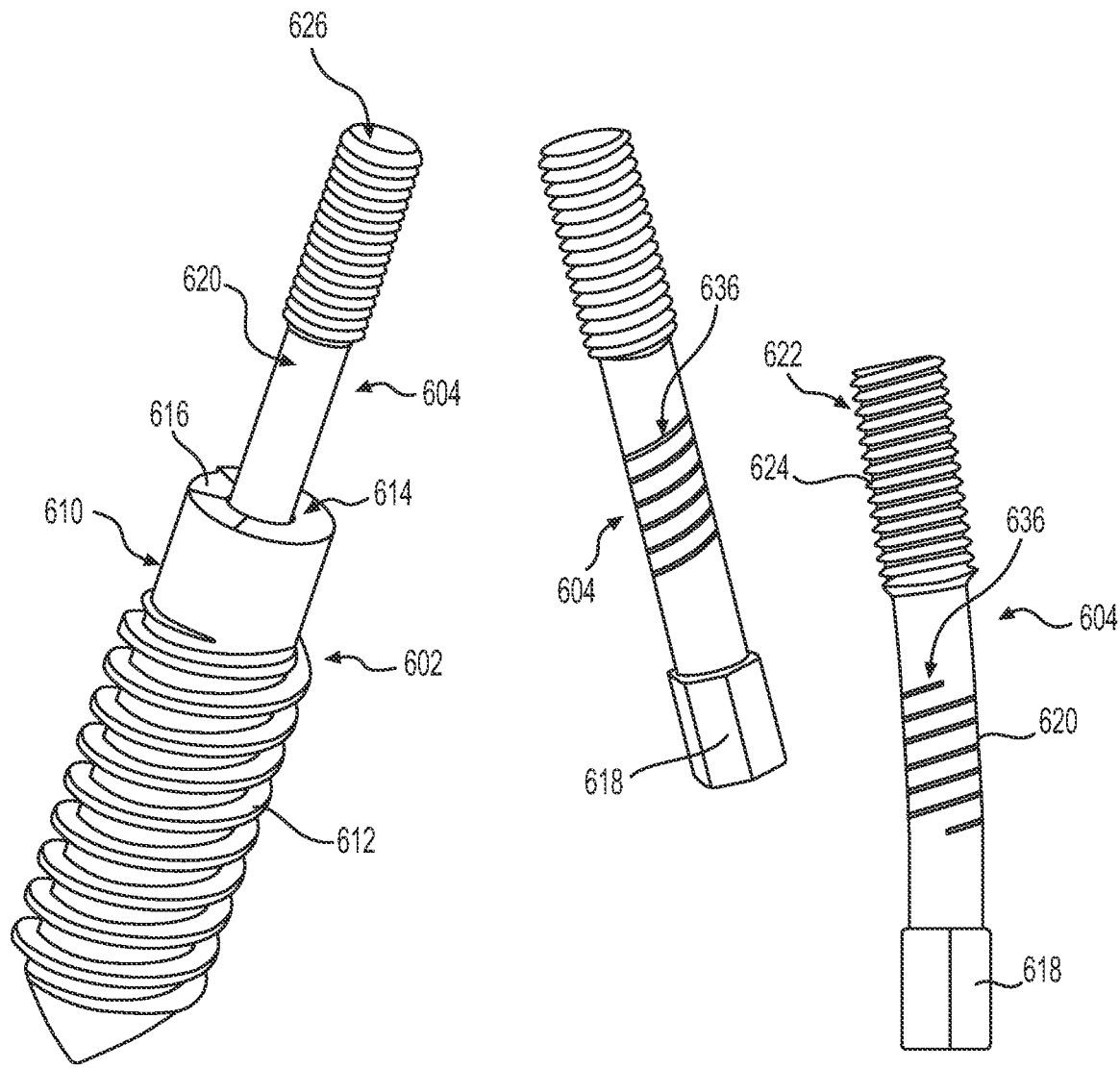
FIG. 13 illustrates a fastener member and torsion member of a spinal stabilization system described herein.
Figure 14:
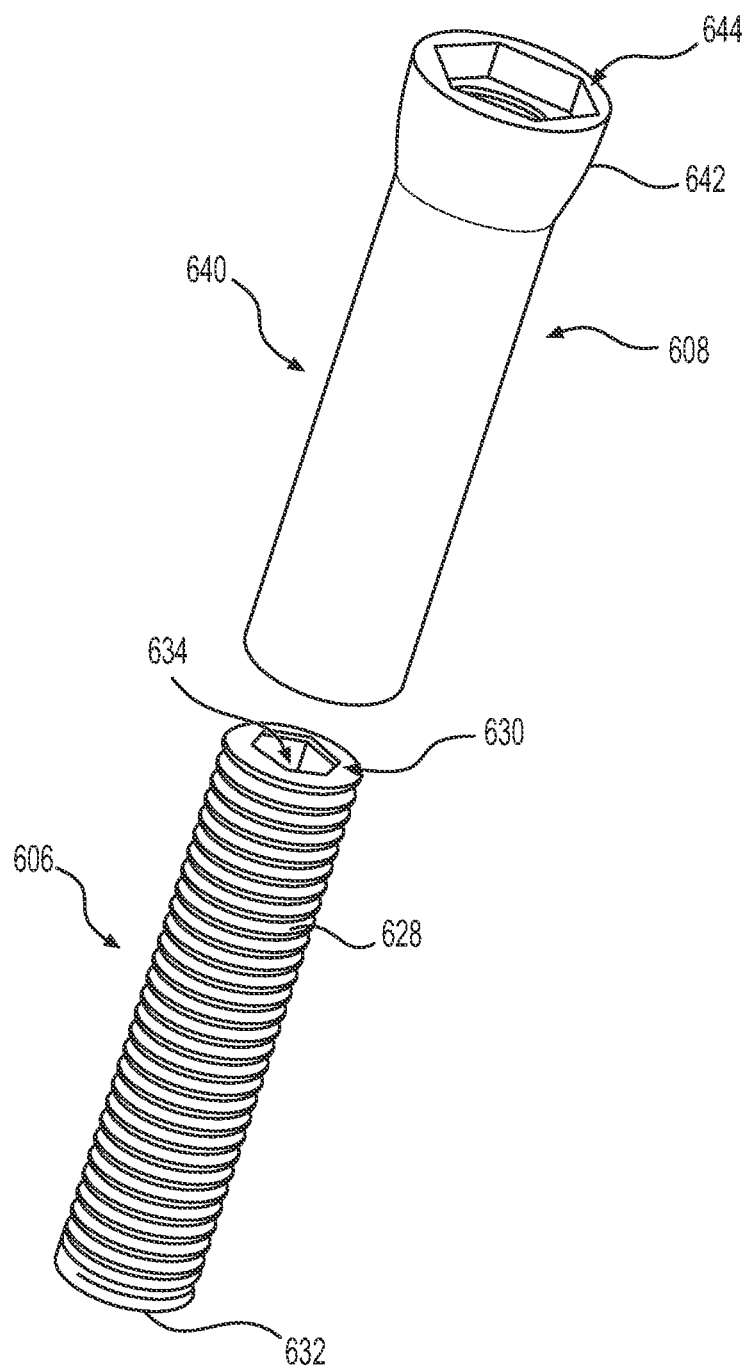
FIG. 14 illustrates a relief member and compression member of a spinal stabilization system described herein.

Turning now to FIGS. 13-17, a spinal stabilization system 600 and its components are illustrated in accordance with embodiments described herein. The stabilization system 600 can include a fastener member 602, a torsion member 604, a relief member 606, and a compression member 608, as illustrated in FIGS. 13-14. As illustrated in FIG. 13, the fastener member 602 can include a head 610, a threaded body or shank 612 extending longitudinally from the head 610, and a socket 614. In some embodiments, the head 610 can include a cylindrical (e.g., constant diameter) outer surface. For example, in some embodiments the head 610 may be referred to as a post. In some embodiments, the head 610 can include a smooth (e.g., non-threaded) exterior surface. In some embodiments where the head 610 includes exterior threading, the threaded head can include a constant major thread diameter and/or a constant minor thread diameter. In embodiments where the head 610 is cylindrical and includes exterior threading, it may be referred to as a threaded post. In some embodiments, the fastener member 602 may be a screw, such as a bone screw. In some embodiments, the fastener member 602 may be referred to as a screw.

As illustrated in FIG. 13, the fastener member 602 can also include a proximal surface 616. The proximal surface 616 may be configured to contact a portion of the relief screw 606, as described further herein. In some embodiments, the proximal surface 616 can be smooth. In other embodiments, the proximal surface 616 can include an engagement feature. As illustrated in FIG. 13, the engagement feature can include a plurality of steps or ratchets that can enhance the interface between the proximal surface 616 of the fastener member and the relief screw 606.

As illustrated in FIG. 15A, the socket 614 can extend through the head 610 and at least partially through the threaded body 612. The shape of the lateral (e.g., transverse) cross-section of the socket 614 can vary, and can include, for example, a circle, oval, slot, star, cross, triangle, square, hexagon, or pentagon. For example, at least a portion of the socket 614 can include a hexagonal lateral cross-section. In some embodiments, the socket 614 can have a lateral cross-sectional shape that varies along a length of the fastener member 602. For example, the socket 614 can have a circular transverse cross-section in the head 610 and an angular transverse cross-section in the threaded body 612. In one embodiment, the socket 614 can have a hexagonal lateral cross-section in the threaded body 612. The diameter or width of the socket 614 can also vary along the length of the fastener member 602. In some embodiments, the diameter or width of the socket 614 can be greater in the threaded body 612 as compared to in the head 610, as illustrated in FIG. 15A.

As illustrated in FIG. 13, the torsion member 604 can include a distal section 618, a body 620, and a proximal section 622. In some embodiments, the torsion member 604 may be referred to as a torsion shaft. The distal section 618 may be configured to be received or disposed within the socket 614 of the fastener member 602. The shape of the lateral (e.g., transverse) cross-section of the torsion member 604 may vary, and can include, for example, a circle, oval, slot, cross, star, triangle, square, hexagon, or pentagon. In some embodiments, the torsion member 604 can have a transverse cross-sectional shape that varies along a length of the torsion member 604. In some embodiments, the distal section 618 can have a hexagonal lateral cross-section and the proximal section 622 and body 620 can each have a circular lateral cross-section. Accordingly, in some embodiments the body 620 can be cylindrical. The size of the lateral cross-section, diameter, or width of the torsion member 604 can also vary along the length of the fastener member. For example, the distal section 618 of the torsion member 604 can include a cross-section, diameter, or width that is greater than a cross-section, diameter, or width of the body 620. In some embodiments, the distal section 618 may be configured to not be rotatable within the socket 614. In other embodiments, the distal section 618 may also be configured to rotate within the socket 614.

In some embodiments, at least a portion of the torsion member 604, such as the body 620, may be flexible (e.g., may be configured to flex, bend, twist, or contort under pressure from one or more vertebrae). The body 620 may be configured to flex using a variety of different techniques. In some embodiments, the body 620 can include at least one incision, opening, notch, slit, or cut 636. In some embodiments, the body 620 can include a plurality of cuts. The cut 636 may include one or more linear (e.g., straight), angular, and/or curved sections. The cut 636 may revolve or rotate about a longitudinal axis. For example, the cut 636 can be a helical cut that extends along a length of the body 620, as illustrated in FIG. 13. In embodiments including a cut, the body 620 may be configured to flex as the result of structural instability that may be generated by the cut 636. In other embodiments, the body 620 can include at least one groove or trench. In yet other embodiments, the body 620 may include a flexible or malleable material. The proximal section 622 can include an externally-threaded portion 624 and/or a tool-receiving recess 626. The tool-receiving recess 626 can be configured to receive a driver, such as a screwdriver or hex key, or other insertion tool. The lateral cross-sectional shape of the recess 626 can vary to accommodate various drivers, and can be, for example, a slot, cross, star, triangle, square, hexagon, or pentagon. In some embodiments, at least a section of the recess 626 can have a hexagonal lateral cross-section.

The relief member 606 can include a body 628. The body 628 can be bounded by a proximal end 630 and a distal end 632, as illustrated in FIG. 14. The relief member 606 can also include a bore 634 extending longitudinally therethrough. The distal end 632 may be configured to contact a portion of the fastener member 602, such as the proximal surface 616, as described further herein. In some embodiments, the distal end 632 can be smooth. In other embodiments, the distal end 632 can include an engagement feature. As illustrated in FIG. 14, the engagement feature can include a plurality of steps or ratchets that can enhance the interface between the proximal surface 616 of the fastener member 602 and the distal end 632 of the relief member 606. In some embodiments, the engagement feature on the distal end 632 of the relief member 606 can mate or mesh with the engagement feature on the proximal surface 616 of the fastener member.

The bore 634 can include a proximal end that includes a tool-receiving recess 638, illustrated in FIG. 15A. The tool-receiving recess 638 can be configured to receive a driver, such as a screwdriver or hex key, or other insertion tool. The lateral cross-sectional shape of the recess 638 can vary to accommodate various drivers, and can be, for example, a slot, cross, star, triangle, square, hexagon, or pentagon. In some embodiments, at least a section of the recess 638 can have a hexagonal lateral cross-section. The bore 634 can include an internally-threaded portion 635 that is configured to mate with the externally-threaded portion 624 of the torsion member 604. The body 628 can also include an externally-threaded portion, as illustrated in FIG. 14. In some embodiments, the relief member 606 can include external threading along its length in one or more sections. In other embodiments, the body 628 can include external threading along its entire length. In embodiments including internal and/or external threading, the relief member 606 may be referred to as a relief screw. The relief member 606 may be cylindrical (e.g., may include a constant outer diameter). In embodiments where the entire body 628 includes exterior threading, the threading may include a constant major diameter and/or a constant minor diameter.

As illustrated in FIGS. 14-15B, the compression member 608 can include a body 640 and a proximal end 642. The body 640 can be elongate and/or cylindrical (e.g., can have a constant outer diameter). The proximal end 642 can have an outer width or diameter that is greater than an outer width or diameter of the body 640. The body 640 can also have an inner and/or outer diameter that is greater than an outer diameter of the relief member 606. Additionally, the proximal end 642 can include a tapered outer surface (e.g., can have an outer diameter that increases or decreases in either the distal or proximal direction).

The compression member 608 can also include a bore 646 extending longitudinally therethrough. As illustrated in FIG. 15A, the bore 646 can include one or more internally-threaded portions 648. In some embodiments, the entire bore can include internal threading (e.g., the bore 646 can include one internally-threaded portion 646 that spans an entire length of the bore 646). The internally-threaded portion 648 can be configured to mate with the externally-threaded portion of the relief member 606. The compression member 608 may be configured to thread onto at least a portion of the relief member 606 and may be referred to as a compression nut. The proximal end 642 can include a tool-receiving recess 644. The tool-receiving recess 644 can be configured to receive a driver, such as a screwdriver or hex key, or other insertion tool. The lateral cross-sectional shape of the recess 644 can vary to accommodate various drivers, and can be, for example, a slot, cross, star, triangle, square, hexagon, or pentagon. In some embodiments, at least a section of the recess 644 can have a hexagonal lateral cross-section.

Embodiments herein are also directed to methods of installing the spinal stabilization system 600. These embodiments may include providing an assembled spinal stabilization system 600. An example of an assembled system is illustrated in FIGS. 15A-B. When assembled, the distal section 618 of the torsion member 604 may be disposed within the socket 614 of the fastener member 602. In some embodiments, the torsion member 604 may be configured to be unremovable from the socket 614 of the fastener member 602. The relief member 606 may be threaded onto the externally-threaded portion 624 of the torsion member 604. The compression member 608 may be threaded onto the externally-threaded portion of the body 628 of the relief member 606. Advantageously, while assembled, all of the tool-receiving recesses 626, 638, 644 may be accessible by a driver, such as a hex key. Additionally, when assembled, all components, and the system 600 overall, may share (e.g., may be configured to rotate about) a longitudinal axis 650. Those skilled in the art may also appreciate that the spinal stabilization system 600 may have a variable length, which can result from translating the compression member 608 along the longitudinal axis 650 relative to the relief member 606. As described further herein, the spinal stabilization system 600 may utilize one or more of these features so as to be configured to compress or shift two bones or fragments thereof together, and may be referred to as a compression system.

Figure 16A:
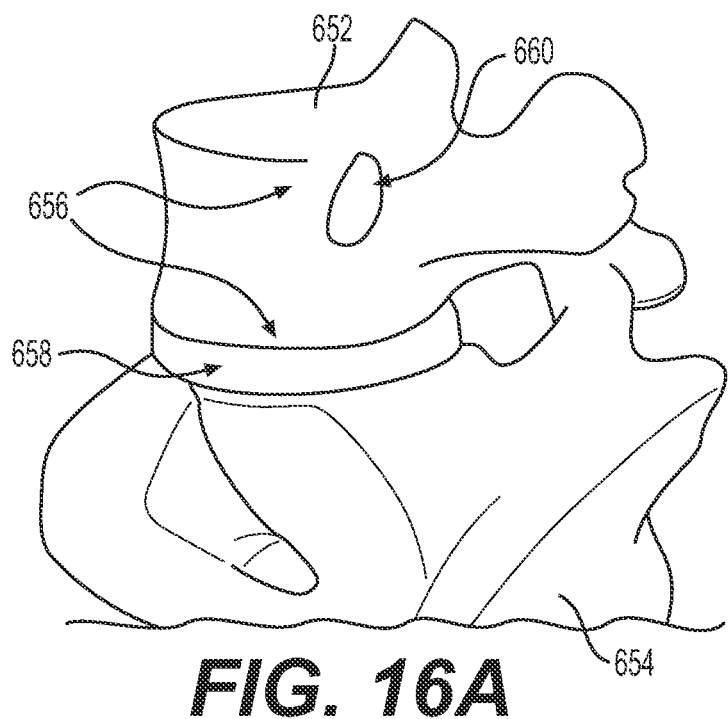
FIGS. 16A-D illustrate a method of installing a spinal stabilization system described herein.

The method can also include creating a passageway 656 at least partially through a proximal fragment or bone 652 and a distal fragment or bone 654, as illustrated in FIG. 16A. The passageway 656 may pass at least partially through a body of the proximal bone 652 and a body of the distal bone 654. The method may be used with any bones or fragments as appropriate. In some embodiments, the proximal and distal bones 652, 654 are adjacent vertebrae, as illustrated in FIG. 16A. In these embodiments, the methods described herein may be used to treat a condition where one or more vertebrae are displaced and/or misaligned, such as spondylolisthesis. In one embodiment, at least one of the proximal bone and the distal bone may be anteriorly displaced prior to the installation of the system.

The passageway 656 may be created using methods known in the art, such as drilling. In some embodiments, the passageway 656 may have a variable diameter. For example, the passageway 656 may have a first section 658 with a first diameter and a second section 660 with a second diameter, wherein the first diameter is smaller than the second diameter. In some embodiments, the first diameter is smaller than the diameter of the proximal end 642 of the compression member 608. In other embodiments, the second diameter may be equal to or greater than the diameter of the proximal end 642. In some embodiments, the diameter of the passageway 656 may be smaller in the distal bone 654 than in the proximal bone 652. In other embodiments, the second section 660 having an enlarged diameter may be disposed within the proximal bone 652.

Figure 16B:
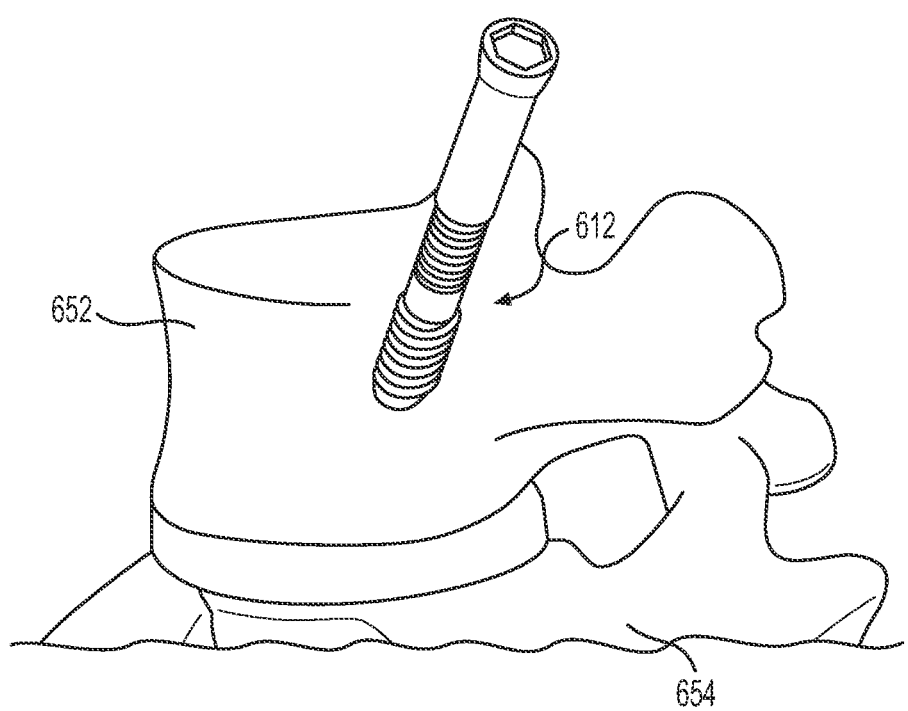

After the passageway 656 is created, the body 612 of the fastener member 602 may be inserted (e.g., threaded) through the passageway 656 into the distal bone 654, as illustrated in FIG. 16B. Torque may be applied to the fastener member 602 by engaging a driver with the tool-receiving recess 638 on the relief member 606. Because the relief member 606 and the fastener member 602 may be engaged via the torsion member 604, the force applied to the relief member 606 may be transferred to the fastener member 602. In some embodiments, the spinal stabilization system 600 may be inserted directly into the passageway 656. In other embodiments, all or a portion of the spinal stabilization system 600 may be inserted through a sheath, tub, or sleeve, and/or over a guide wire. Advantageously, the spinal stabilization system 600 may be configured to be installed in a minimally-invasive and/or percutaneous procedure.

Figure 16C:
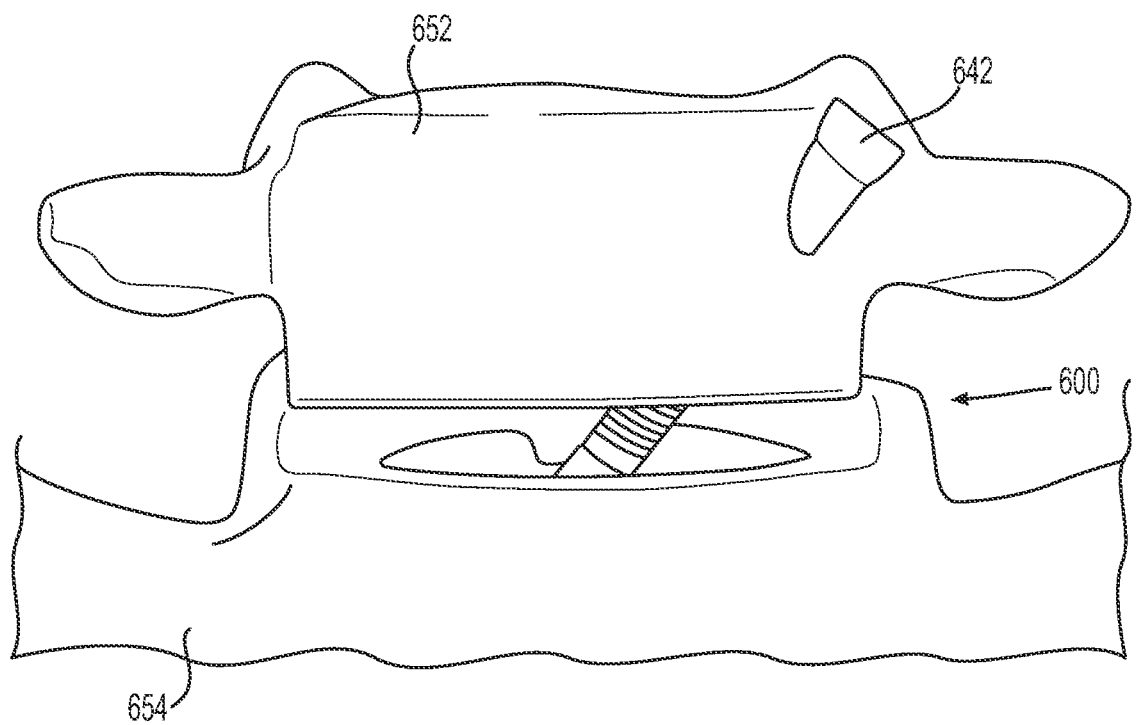

After the fastener member 602 is inserted into the distal bone 654, the compression member 608 may be inserted (e.g., threaded) into the proximal bone 652, as illustrated in FIG. 16C. Torque may be applied to the compression member 608 by engaging a driver with the tool-receiving recess 644. As described herein, the passageway 656 may have an enlarged section at a proximal end of the passageway 656. In use, as the compression member 608 is inserted into the proximal bone 652, the enlarged proximal end 642 may be inserted into the enlarged section 660 of the passageway 656, but may not fit within the smaller section 658 of the passageway 656. As the proximal end 642 abuts the smaller section 658 of the passageway 656, the torque applied by a driver may advantageously result in reducing the overall length of the system 600, thereby pulling or compressing the relief member 606 and compression member 608 components towards each other. Accordingly, when the fastener member 602 is secured within the distal bone 654, the action of driving the compression member 608 through the passageway 656 may result in pulling the proximal and distal bones 652, 654 towards each other to alter the relative alignment between the two bones. As described herein, this method may advantageously be used to treat conditions where one or more bones have been displaced, such as spondylolisthesis.

Figure 16D:
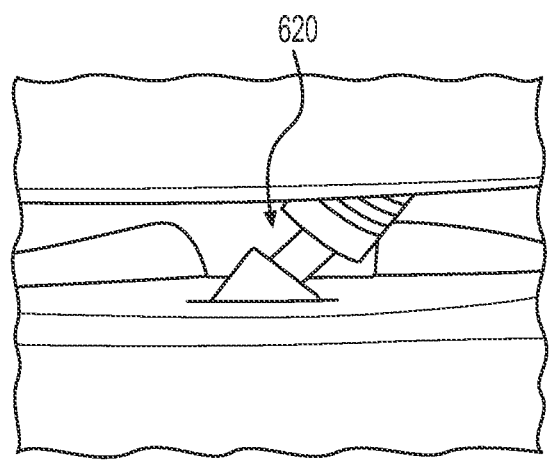

In some embodiments, the methods described herein can further include exposing at least a portion of the torsion member 604, such as the body 620, as illustrated in FIG. 16D. This step can include at least partially disengaging (e.g., unthreading) the relief member 606 from the torsion member 604. This may be accomplished by coupling a driver with the tool-receiving recess 638 and applying torque to the relief member 606. Advantageously, when the body 620 is exposed, it may allow the spinal stabilization system 600 to bend, flex, and/or twist, thereby relieving pressure on adjacent structures (e.g., facet joints). In some embodiments, the torsion member 604 may also be rotated, twisted, or untwisted, for example, by applying torque at the tool-receiving recess 626. Advantageously, this step may reduce the axial load on the torsion member 604.

In other embodiments, the spinal stabilization system 600 may be at least partially assembled during the installation process (e.g., may not be fully assembled when the installation process begins). As one example, the torsion member 604 and the fastener member 602 may be assembled as illustrated in FIG. 13 and inserted into a bone. Thereafter, the relief member 606 may be threaded onto the torsion member 604, and the compression member 608 may subsequently be threaded onto the relief member 606. In another embodiment, the fastener member 602, torsion member, and relief member 606 may be assembled prior to installation, and the compression member 608 may be threaded on to the relief member 606 in situ. Those skilled in the art may appreciate that other variations on the order of assembly and implantation may also be used. Advantageously, these variations may be applied minimally-invasively.

Figure 17:
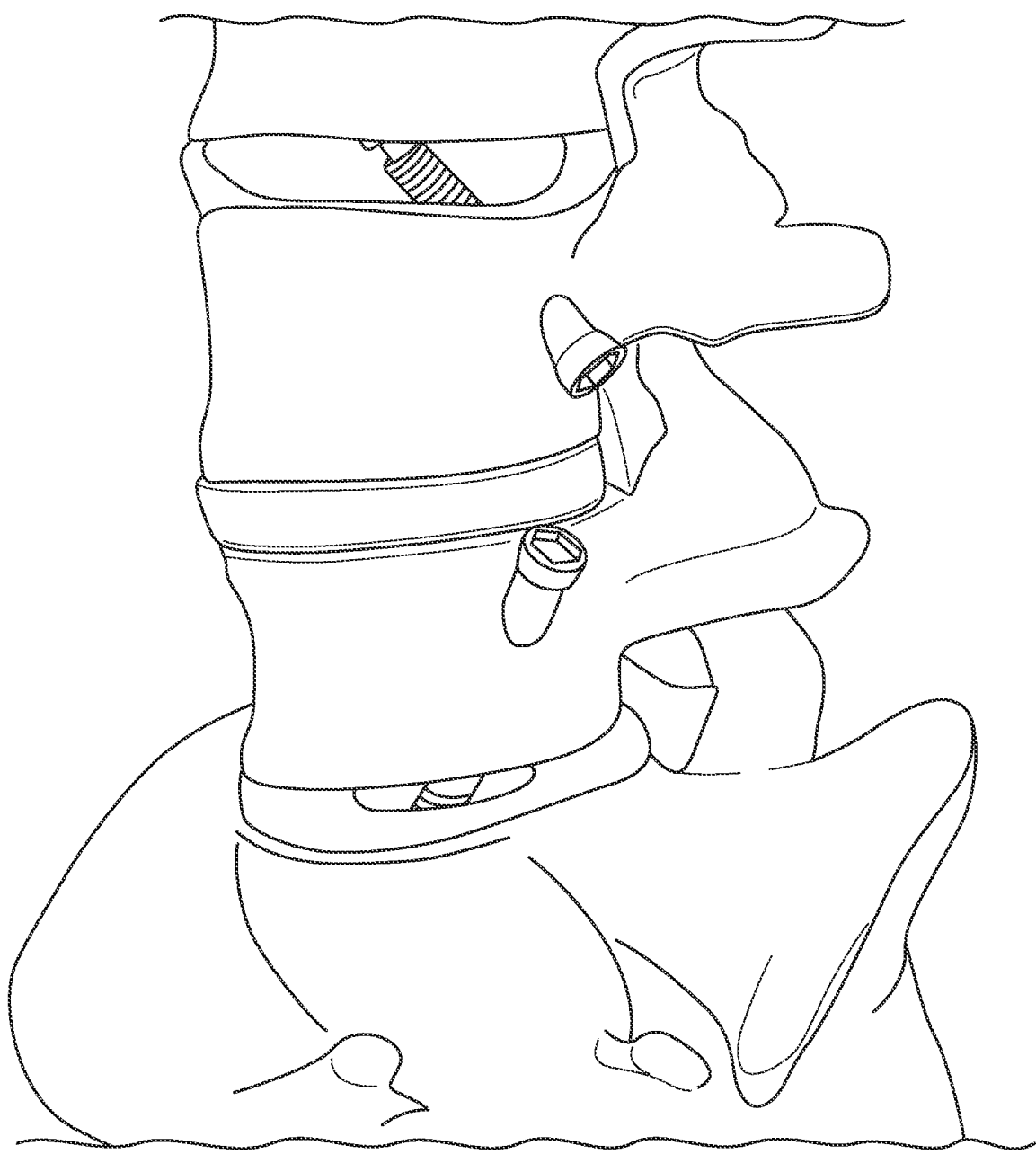
FIG. 17 illustrates multiple spinal stabilization systems installed in a spine.

In some embodiments, multiple spinal stabilization systems 600 may be installed in a spine, as illustrated in FIG. 17. The number and placement of the spinal stabilization systems 600 may vary, for example, on the extent and/or orientation of the vertebral displacement. As described herein, the spinal stabilization system 600 may advantageously be used to treat vertebral displacement conditions, such as spondylolisthesis, with a single device that can be installed in a minimally-invasive or percutaneous procedure.

Any of the devices described above can be part of a larger spinal stabilization system including, but not limited to, any of the following: rod members, screw members (including polyaxial and uniplanar screws), plate members, spacers and cages. In addition, the devices described above can be used in conjunction with fusion devices and prosthetic devices, such as artificial discs and artificial facet joint prostheses. Furthermore, the devices can be accompanied by natural and synthetic biological material, such as bone graft material.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. A method of implanting a spinal stabilization system, the method comprising:
    providing an assembled spinal stabilization system comprising:
        a fastener assembly, the fastener assembly comprising a fastener member and a compression member, the fastener member and the compression member defining a longitudinal axis;

a clamp assembly, the clamp assembly comprising a coupling member, a clamp member, and at least one locking member;

wherein the coupling member includes a stabilization member receiving portion, a fastener assembly receiving opening, and a locking member receiving opening, wherein the stabilization member receiving portion is laterally offset from the fastener assembly receiving opening, wherein the locking member receiving opening is laterally spaced apart from the stabilization member receiving portion and laterally spaced apart from the fastener assembly receiving opening, wherein the locking member receiving opening does not overlap the fastener assembly receiving opening, creating a passageway at least partially through a proximal bone and a distal bone, wherein a proximal end of the passageway includes an enlarged section;

inserting a body of the fastener member through the passageway and into the distal bone; and inserting the compression member through the passageway and into the proximal bone wherein the assembled stabilization system further comprises a second locking member, wherein the coupling member includes a second locking member opening for receiving the second locking member.

2. The method of claim 1, wherein the fastener member includes a threaded shank and wherein a second socket is configured for receiving an insertion tool.

3. The method of claim 1, wherein the compression member includes a body portion extending from an enlarged head.

4. The method of claim 3, wherein the body portion of the compression member includes a bore for receiving a head portion of the fastener member.

5. The method of claim 4, wherein the enlarged head of the compression member includes a rounded outer surface and includes a socket for receiving an insertion tool.

6. The method of claim 5, wherein, while the compression member and fastener member are assembled, first and second sockets are accessible by a driver.

7. The method of claim 5, wherein the clamp member includes an inner surface and an outer surface, the inner surface is configured to receive the enlarged head of the compression member.

8. The method of claim 7, wherein the outer surface of the clamp member is rounded to form at least in part a generally spherical outer surface.

9. The method of claim 8, wherein clamp member is received within the fastener assembly receiving opening of the coupling member and wherein the fastener assembly is capable of polyaxial movement with respect to the coupling member.

10. The method of claim 7, wherein the clamp member includes at least one slot to allow the clamp member to expand or contract radially.

11. The method of claim 1, the locking member receiving opening is in fluid communication with the fastener assembly receiving opening.

12. The method of claim 11, wherein the locking member engages the outer surface of the clamp member positioned in the fastener assembly receiving opening.

13. The method of claim 12, wherein the locking member locks the clamp member in place preventing polyaxial movement of the fastener assembly with respect to the coupling member.

14. The method of claim 1, wherein the second locking member locks the coupling member to a spinal stabilization member.

* * * * *